United States Patent
Griessner et al.

(10) Patent No.: US 10,597,703 B2
(45) Date of Patent: Mar. 24, 2020

(54) ANALYSIS SYSTEM AND METHOD FOR TESTING A SAMPLE

(71) Applicant: Boehringer Ingelheim Vetmedica GmbH, Ingelheim am Rhein (DE)

(72) Inventors: Matthias Griessner, Hannover (DE); Heinz Schoeder, Isernhagen (DE)

(73) Assignee: BOEHRINGER INGELHEIM VETMEDICA GMBH, Ingelheim am Rhein (DE)

( * ) Notice: Subject to any disclaimer, the term of this patent is extended or adjusted under 35 U.S.C. 154(b) by 0 days.

(21) Appl. No.: 15/725,332

(22) Filed: Oct. 5, 2017

(65) Prior Publication Data

US 2018/0100188 A1 Apr. 12, 2018

(30) Foreign Application Priority Data

Oct. 7, 2016 (EP) .................................... 16020373

(51) Int. Cl.
| | | |
|---|---|---|
| *C12Q 1/6825* | (2018.01) | |
| *B01L 3/00* | (2006.01) | |
| *G01N 27/327* | (2006.01) | |
| *G01N 33/543* | (2006.01) | |
| *B01L 7/00* | (2006.01) | |

(52) U.S. Cl.
CPC .......... *C12Q 1/6825* (2013.01); *B01L 3/5027* (2013.01); *G01N 27/3277* (2013.01); *G01N 33/5438* (2013.01); *B01L 7/52* (2013.01); *B01L 2300/0636* (2013.01); *B01L 2300/0819* (2013.01); *B01L 2300/18* (2013.01)

(58) Field of Classification Search
CPC .. C12Q 1/6825; G01N 33/5438; C12M 41/28
See application file for complete search history.

(56) References Cited

U.S. PATENT DOCUMENTS

| | | | |
|---|---|---|---|
| 5,096,669 A | 3/1992 | Lauks et al. | |
| 7,914,655 B2 | 3/2011 | Frey et al. | |
| 8,597,574 B2 | 12/2013 | Gumbrecht et al. | |
| 8,741,815 B2 | 6/2014 | Gordon et al. | |
| 9,110,044 B2 | 8/2015 | Gumbrecht et al. | |
| 9,651,568 B2 | 5/2017 | Putnam et al. | |
| 9,797,894 B2* | 10/2017 | Kumar | G01N 33/54386 |
| 2003/0064507 A1 | 4/2003 | Gallagher et al. | |
| 2005/0196756 A1 | 9/2005 | Schmidt et al. | |
| 2007/0148678 A1 | 6/2007 | Ehben et al. | |
| 2009/0057147 A1* | 3/2009 | Kayyem | B01L 3/5027 204/403.01 |
| 2009/0325276 A1 | 12/2009 | Battrell et al. | |
| 2012/0282602 A1* | 11/2012 | Drader | G01N 27/3273 435/6.1 |
| 2013/0067525 A1 | 3/2013 | Wang | |
| 2013/0203057 A1 | 8/2013 | Lemieux et al. | |
| 2013/0316340 A1* | 11/2013 | Kelley | G01N 33/5438 435/6.11 |
| 2015/0141272 A1* | 5/2015 | Gordon | C12Q 1/6804 506/9 |
| 2015/0292005 A1* | 10/2015 | Tomita | C12Q 1/6816 506/9 |
| 2016/0298178 A1 | 10/2016 | Lammertyn et al. | |

FOREIGN PATENT DOCUMENTS

| | | | |
|---|---|---|---|
| EP | 1 947 197 A1 | | 7/2008 |
| GB | 2 436 616 A | | 10/2007 |
| WO | WO 2015/054546 | * | 4/2015 |

OTHER PUBLICATIONS

Harper et al, Selective Immobilization of DNA and Antibody Probes on Electrode Arrays: Simultaneous Electrochemical Detection of DNA and Protein on a Single Platform, 2007, Langmuir, 23, 8285-8287 (Year: 2007).*

Harper et al, Selective Immobilization of DNA and Antibody Probes on Electrode Arrays: Simultaneous Electrochemical Detection of DNA and Protein on a Single Platform, 2007, Langmuir, 23, 8285-8287—supplemental information, pp. 1-5. (Year: 2007).*

Christos Kokkinos, Anastasios Economou, Mamas I. Prodromidis; Electrochemical Immunosensors: Critical Survey of Different Architectures and Transduction Stragegies, Trends in Analytical Chemistry, BD. 79, May 1, 2016 (May 1, 2016), p. 88-105, XP055355665, Amsterdam, NL.

* cited by examiner

*Primary Examiner* — Narayan K Bhat
(74) *Attorney, Agent, or Firm* — David S. Safran; Roberts Calderon Safran & Cole, P.C.

(57) ABSTRACT

An analysis system and a method for testing a biological sample wherein a plurality of assays selected from at least two assays from a group consisting of a protein assay for detecting a target protein, a nucleic-acid assay for detecting a target nucleic-acid sequence and/or an aptamer assay for detecting another target analyte, The testing is carried out sequentially in a common sensor array by means of a sensor apparatus.

28 Claims, 13 Drawing Sheets

ANALYSIS SYSTEM AND METHOD FOR TESTING A SAMPLE

BACKGROUND OF THE INVENTION

Field of the Invention

The present invention relates to an analysis system and a method for testing a biological sample.

Preferably, the present invention deals with analyzing and testing a sample, in particular from a human or animal, particularly preferably for analytics and diagnostics, for example with regard to the presence of diseases and/or pathogens and/or for determining blood counts, antibodies, hormones, steroids or the like. Therefore, the present invention is in particular within the field of bioanalytics. A food sample, environmental sample or another sample may optionally also be tested, in particular for environmental analytics or food safety and/or for detecting other substances.

Preferably, by means of the present invention, at least one analyte (target analyte) of a sample can be identified, determined or detected. In particular, the sample can be tested for qualitatively or quantitatively determining at least one analyte, for example in order for it to be possible to detect or identify a disease and/or pathogen.

Within the meaning of the present invention, analytes are in particular nucleic-acid sequences, in particular DNA sequences and/or RNA sequences, or proteins, in particular antigens and/or antibodies, or other analytes, in particular hormones, low-molecular substances, steroids, organophosphates or the like. In particular, by means of the present invention, nucleic-acid sequences can be determined or detected as analytes of a sample, proteins can be determined or detected as analytes of the sample, or other analytes of the sample can be determined or detected. More particularly preferably, the present invention deals with systems, devices and other apparatuses for carrying out a nucleic-acid assay for detecting a nucleic-acid sequence, a protein assay for detecting a protein, or an aptamer assay for detecting a protein, a low-molecular substance, a steroid, an organophosphate or other target analytes.

The present invention deals in particular with what are known as point-of-care systems, i.e., in particular with mobile systems, devices and other apparatuses, and deals with methods for carrying out tests on a sample at the sampling site and/or separately or away from a central laboratory or the like. Preferably, point-of-care systems can be operated autonomously or independently of a mains network for supplying electrical power.

Description of Related Art

U.S. Pat. No. 5,096,669 discloses a point-of-care system for testing a biological sample, in particular a blood sample. The system comprises a single-use cartridge and an analysis device. Once the sample has been received, the cartridge is inserted into the analysis device in order to carry out the test. The cartridge comprises a microfluidic system and a sensor apparatus comprising electrodes, which apparatus is calibrated by means of a calibration liquid and is then used to test the sample.

Furthermore, International Patent Application Publication WO 2006/125767 A1 and corresponding U.S. Pat. No. 9,110,044 disclose a point-of-care system for integrated and automated DNA or protein analysis, comprising a single-use cartridge and an analysis device for fully automatically processing and evaluating molecular-diagnostic analyzes using the single-use cartridge. The cartridge is designed to receive a sample, in particular blood, and in particular allows cell disruption, PCR and detection of PCR amplification products, which are bonded to capture molecules and provided with a label enzyme, in order for it to be possible to detect bonded PCR amplification products or nucleic-acid sequences as target analytes in what is known as a redox cycling process.

U.S. Patent Application Publication 2014/0377852 A1 discloses a microfluidic device for performing protein assays and/or nucleic acid assays, wherein glass nano-reactors formed by functionalized micro-length tubes are used for optical detection. The glass nano-reactors can be made with captures strands complementary to a sequence of interest. Multiple different populations of glass nano-reactors, specific for different DNA target populations can be used.

SUMMARY OF THE INVENTION

The problem addressed by the present invention is to provide an improved analysis system and an improved method for testing a sample, a simple and/or compact construction or design of the analysis system and/or comprehensive, efficient, rapid, reliable and/or precise testing of the sample, in particular at a high sample throughput, preferably being made possible or facilitated thereby.

The above problem is solved by an analysis system according to claim 1 or by a method according to claim 14. Advantageous developments are the subject of the dependent claims.

The proposed analysis system for testing an in particular biological sample preferably comprises a sensor apparatus and in particular a cartridge comprising a sensor apparatus for identifying or detecting—preferably multiple different— analytes of the sample, the cartridge and/or sensor apparatus preferably being provided with capture molecules for capturing and/or bonding the analytes.

One aspect of the present invention is that the sensor apparatus—preferably a sensor array thereof—comprises a plurality of types of capture molecules, the capture molecules being selected from a selection group consisting of capture proteins, capture aptamers and/or capture nucleic-acid sequences, in particular in order to bond target analytes, in particular target proteins and/or target hormones, which correspond to the capture proteins, to bond target analytes, in particular target nucleic-acid sequences, which correspond to the capture nucleic-acid sequences, and/or to bond target analytes, in particular target proteins, low-molecular substances, steroids, organophosphates or other target analytes, which correspond to the capture aptamers.

According to a first embodiment, the sensor apparatus comprises both capture proteins and capture nucleic-acid sequences as capture molecules, in particular in order to bond target analytes, in particular target proteins and/or target hormones, which correspond to the capture proteins, and to bond target analytes, in particular target nucleic-acid sequences, which correspond to the capture nucleic-acid sequences.

According to another embodiment, the sensor apparatus comprises both capture aptamers and capture nucleic-acid sequences as capture molecules, in particular in order to bond target analytes, in particular target proteins, low-molecular substances, steroids, organophosphates or other target analytes, which correspond to the capture aptamers, and to bond target analytes, in particular target nucleic-acid sequences, which correspond to the capture nucleic-acid sequences.

Particularly preferably, capture proteins are used as the capture molecules. Capture aptamers can preferably be used alternatively or in addition as capture molecules, in particular as a group of capture molecules in a manner corresponding to the capture proteins. The following explanations therefore in particular also apply accordingly or additionally to capture aptamers as capture molecules.

According to another embodiment, the sensor apparatus comprises both capture proteins and capture aptamers as capture molecules, in particular in order to bond target analytes, in particular low-molecular substances, steroids, organophosphates or other target analytes, which correspond to the capture aptamers, and to bond target analytes, in particular target proteins, which correspond to the capture proteins.

According to another, particularly preferred embodiment, the sensor apparatus comprises capture proteins, capture aptamers and capture nucleic-acid sequences.

According to another aspect of the present invention, which can also be implemented independently, the analysis system and/or the cartridge and/or sensor apparatus is designed to carry out a plurality of (different) assays, in particular sequentially, the assays preferably being selected from a selection group consisting of a protein assay for detecting a target analyte, in particular a target protein, particularly preferably by means of a capture protein, a nucleic-acid assay for detecting a target analyte, in particular a target nucleic-acid sequence, particularly preferably by means of a capture nucleic-acid sequence, and/or an aptamer assay for detecting a target analyte, in particular a target protein or another target analyte that is preferably different from the target protein, particularly preferably by means of a capture aptamer.

The sensor apparatus or its sensor array preferably comprises a plurality of sensor fields and/or electrode pairs which each permit independent measurement and/or detection.

Preferably, the—in particular some or all—sensor fields and/or electrode pairs or individual electrodes are each provided with different types of capture molecules, the capture molecules being selected from a selection group consisting of capture proteins, capture aptamers and/or capture nucleic-acid sequences. A plurality of (different) assays and/or detection processes can thus be carried out in succession using the same sensor fields and/or electrode pairs. This allows a simple, compact and/or cost-effective construction and allows testing and/or detection of many different target analytes.

Particularly preferably, the sensor fields and/or electrode pairs or individual electrodes are each provided with both capture proteins and capture nucleic-acid sequences. In this way, a protein assay and a nucleic-acid assay can be carried out, in particular sequentially, preferably the target analytes, target proteins and/or capture proteins preferably being denatured only after the target analytes and/or target proteins have been detected and/or after the protein assay has been carried out, before target nucleic-acid sequences are detected and/or the nucleic-acid assay is carried out.

Alternatively, the sensor fields and/or electrode pairs can each be provided only with either capture proteins or capture nucleic-acid sequences. If the sensor fields and/or electrode pairs allow independent measurements, the above-mentioned denaturing of target proteins and/or capture proteins, which also results in denaturing or detaching of target proteins bonded thereto, can be omitted. In particular, measuring errors and/or detection errors are in any case minimized, since any capture proteins and/or target proteins that may (still) be present do not influence the measurement of target nucleic-acid sequences and/or do not have any influence when the nucleic-acid assay is being carried out.

Particularly preferably, the analysis system and/or an analysis device of the analysis system comprises a temperature-control apparatus for temperature-controlling the sensor apparatus or a sensor arrangement formed thereby and/or the cartridge and/or a fluid contained therein such that the target proteins and/or capture proteins are deactivated and/or denatured by means of a corresponding effect of heat, in particular by heating to above 40° C. or 50° C., and/or the capture nucleic-acid sequences and target nucleic-acid sequences that are bonded to one another are separated from one another by means of a corresponding effect of heat, in particular by heating to above 90° C. or 95° C., and/or the capture aptamers are thermally activated and/or folded by means of a corresponding effect of heat, in particular by heating to above 90° C. or 95° C.

The term "denaturing" is preferably understood to mean a structural change to molecules, in particular proteins and/or nucleic-acid sequences. During denaturing, the spatial structure and/or 3D structure of the molecules is preferably destroyed. Denaturing in particular results in the bond between the capture proteins and target proteins or between the capture nucleic-acid sequences and target nucleic-acid sequences being broken.

Denaturing is preferably brought about by the effect of heat. Denaturing can, however, also be brought about by other physical influences and/or by chemical influences.

Denaturing can in particular result from a direct effect of heat, for example from directly heating the sensor apparatus, and/or from an indirect effect of heat, for example from feeding a heated fluid.

Denaturing of the capture proteins and/or the target proteins preferably occurs after the protein assay has been carried out, i.e. after target proteins have been detected.

A flushing or washing process preferably occurs after denaturing, in order to prepare the cartridge and/or sensor apparatus for the next detection and/or for the nucleic-acid assay.

According to another aspect of the present invention, which can also be implemented independently, the cartridge and/or sensor apparatus preferably comprises a first group of capture molecules, the capture molecules being able to be either thermally blocked and/or denatured, or thermally activated, in particular by heating, in particular by means of a temperature-control apparatus.

Blocking and/or denaturing can prevent bonding of corresponding analytes, in particular after an assay has been carried out, in particular in order to then carry out another assay. Capture proteins can be used as heat-sensitive capture molecules for example, which molecules can be blocked from analyte bonding by means of denaturing, as described above.

On account of the thermal activation and/or folding, it is possible in particular to achieve bonding of corresponding capture molecules to corresponding analytes only after the thermal activation and/or folding. The thermal activation is carried out in particular by heating to above a specified threshold temperature. In particular, capture aptamers can be used as thermally activatable capture molecules, which aptamers fold and/or convert into a bonding conformation preferably only after the threshold temperature has been reached or exceeded, in order to only subsequently bond corresponding analytes. This means that only heating results in the bondable formation and/or the development of conformation of the capture molecules. The heating is preferably carried out again by means of the temperature-control apparatus.

Preferably, in general a first group of capture molecules can thus be used that are either blocked and/or denatured by a thermal effect and/or heating, or are only activated by a thermal effect and/or heating. In particular, an assay, for example a protein assay or aptamer assay, is then carried out using the first group of capture molecules, and another assay, for example a nucleic-acid assay, is carried out using a second group of (different) capture molecules.

According to another aspect of the present invention, which can also be implemented independently, a plurality of (different) assays are carried out, in particular sequentially or in succession, preferably in one (single) cartridge and/or sensor apparatus, in particular in a common or the same sensor array and/or sensor field of the sensor apparatus.

Particularly preferably, a plurality of assays are carried out, selected from at least two assays from the selection group consisting of a protein assay for detecting a target analyte, in particular a target protein or target hormone, particularly preferably by means of a capture protein, and/or a nucleic-acid assay for detecting a target analyte, in particular a target nucleic-acid sequence, particularly preferably by means of a capture nucleic-acid sequence, and/or an aptamer assay for detecting a target analyte, in particular a target protein and/or another target analyte that is preferably different from the target protein, particularly preferably by means of a capture aptamer, the protein assay preferably being carried out before the nucleic-acid assay, and/or the nucleic-acid assay preferably being carried out before the aptamer assay. This makes comprehensive, rapid and/or precise testing of the sample possible.

In particular, a protein assay and/or an aptamer assay for detecting a target analyte or target protein as the analyte and a nucleic-acid assay for detecting a target nucleic-acid sequence as the analyte are carried out successively or sequentially in a (single) cartridge and/or sensor apparatus. However, other target analytes, such as low-molecular substances, steroids, organophosphates or the like, can also be detected, in particular by means of the aptamer assay.

According to another, particularly preferred variant of the method, a protein assay for detecting a first target analyte, in particular a target protein as the analyte, and an aptamer assay for detecting a second target analyte that is different from the first target analyte, such as a low-molecular substance, a steroid, an organophosphate or the like, are carried out sequentially, the protein assay preferably being carried out before the aptamer assay.

Particularly preferably, target proteins that are immobilised and/or bonded to capture proteins are denatured and/or detached by the effect of heat, in particular by heating the sensor apparatus and/or by feeding in a heated fluid, before the nucleic-acid assay is carried out and/or in order for said assay to be carried out, and/or capture nucleic-acid sequences and target nucleic-acid sequences that are bonded to one another are separated from one another by the effect of heat, in particular by heating the sensor apparatus and/or by feeding in a heated fluid, before the aptamer assay is carried out and/or in order for said assay to be carried out. This results in corresponding advantages.

According to another aspect of the present invention, which can also be implemented independently, both target proteins and target nucleic-acid sequences, as analytes of the sample, are bonded to corresponding capture molecules in a single cartridge and/or in a common sensor apparatus, particularly preferably on a common sensor array, and are detected identified. This makes comprehensive, rapid and/or precise testing of the sample possible.

According to another aspect of the present invention, which can also be implemented independently, the sample is split into portions, in particular in a cartridge, a plurality of (different) assays selected from at least two assays from the selection group consisting of a protein assay, an aptamer assay and/or a nucleic-acid assay being carried out in the same cartridge and/or sensor apparatus. This makes comprehensive, rapid and/or precise testing of the sample possible.

The analysis device and/or the cartridge and/or the sensor apparatus is preferably designed for carrying out a protein assay, aptamer assay and/or nucleic-acid assay. In particular, the sensor apparatus comprises capture proteins as capture molecules, capture nucleic-acid sequences as capture molecules, and/or capture aptamers as capture molecules, in particular in order to bond target analytes, in particular target proteins, which correspond to the capture proteins, to bond target analytes, in particular target nucleic-acid sequences, which correspond to the capture nucleic-acid sequences, and/or to bond target analytes, in particular target proteins or other target analytes, which correspond to the capture aptamers.

The sensor arrangement or sensor apparatus is preferably designed for electrochemically detecting analytes bonded to the capture molecules.

The sensor apparatus preferably comprises (exactly) one sensor array having a plurality of sensor fields and/or electrodes (electrode pairs), the sensor fields and/or electrodes (electrode pairs) in particular each being provided with capture molecules.

Within the meaning of the present invention, capture molecules are in particular nucleic-acid sequences, in particular DNA sequences, RNA sequences and/or aptamers, and/or proteins, in particular antigens and/or antibodies. In particular, capture molecules are designed to bond and/or immobilise corresponding analytes of the sample.

Within the meaning of the present invention, capture nucleic-acid sequences are in particular capture molecules based on long (single-stranded) nucleic-acid sequences, in particular DNA sequences and/or RNA sequences, particularly preferably having more than 70 or 80 bases and/or fewer than 5000 or 1000 bases. In particular, capture nucleic-acid sequences are designed to bond corresponding target nucleic-acid sequences, in particular target DNA sequences and/or target RNA sequences, which are particularly preferably at least substantially of the same length.

Within the meaning of the present invention, capture aptamers are in particular capture molecules based on short (single-stranded) nucleic-acid sequences, particularly preferably having at least 10 or 20 bases and/or at most 70 or 80 bases. Particularly preferably, capture aptamers are shorter than capture nucleic-acid sequences and/or capture aptamers have fewer bases than capture nucleic-acid sequences. Capture aptamers are preferably designed to bond target proteins, low-molecular substances, steroids, organophosphates and/or other target analytes. In particular, within the meaning of the present invention, capture aptamers are DNA oligonucleotides and/or RNA oligonucleotides and/or peptides.

Capture aptamers are preferably produced synthetically and generally do not (yet) have a three-dimensional structure (immediately) after being produced. Against this background, it may be necessary for capture aptamers to first be thermally activated before being used and/or in order to bond target analytes, and/or it may be necessary for the hydrogen bridge bonds to be opened by the effect of heat and formed by subsequent cooling (folding). The capture aptamers thus assume a three-dimensional structure which makes target analyte bonding possible. The temperature for activating and/or folding the capture aptamers (threshold temperature) is preferably greater than 70° C. or 80° C., in particular greater than 90° C. or 95° C. The capture molecules are in particular applied to and immobilised on and/or bonded to the sensor array, in particular the sensor fields and/or electrodes, in a process known as spotting.

In particular, the sensor fields and/or electrodes each comprise at least two types of capture molecules, selected from the selection group consisting of capture proteins, in particular in the form of antibodies, capture nucleic-acid sequences, in particular in the form of preferably single-stranded DNA probes, and/or capture aptamers. For this purpose, in a preferred manner, the capture proteins, capture nucleic-acid sequences and/or capture aptamers are immobilized on the sensor apparatus, in particular on the sensor array and/or the sensor fields, as a mixture. The capture proteins, capture nucleic-acid sequences and/or capture aptamers can bond and/or immobilize analytes based on target proteins, target nucleic-acid sequences and/or other target analytes. The immobilized analytes can be identified or detected by means of subsequent electrochemical measurement and/or redox cycling, and/or fluorescence measurement.

According to the present invention, the analysis system and/or the cartridge and/or the sensor apparatus makes particularly comprehensive testing of the sample possible, in particular the detection of target proteins, target nucleic-acid sequences and/or other target analytes. Thus, a particularly large number of and/or particularly different and/or comprehensive tests can advantageously be carried out on the sample and/or a plurality of diseases and/or pathogens can be detected or identified in the sample.

The analysis system is preferably portable, mobile and/or is a point-of-care system and/or can be used in particular at the sampling site and/or away from a central laboratory and/or can be operated autonomously and/or independently of the mains, in particular independently of a mains power supply, for example by accumulators, batteries and/or other power storage means.

The analysis system preferably comprises an analysis device and a cartridge for testing the sample, the cartridge preferably being designed for receiving the sample and the analysis device preferably being designed for receiving the cartridge.

The term "analysis device" is preferably understood to mean an instrument which is in particular mobile and/or can be used on site, and/or which is designed to chemically, biologically and/or physically test and/or analyze a sample or a component thereof, preferably in and/or by means of a cartridge. In particular, the analysis device controls the pretreatment and/or testing of the sample in the cartridge.

Particularly preferably, the analysis device is designed to receive the cartridge or to connect said cartridge electrically, thermally, mechanically and/or pneumatically.

The term "cartridge" is preferably understood to mean a structural apparatus or unit designed to receive, to store, to physically, chemically and/or biologically treat and/or prepare and/or to measure a sample, preferably in order to make it possible to detect, identify or determine at least one analyte, in particular a protein, a nucleic-acid sequence and/or another analyte, of the sample.

A cartridge within the meaning of the present invention preferably comprises a fluid system having a plurality of channels, cavities and/or valves for controlling the flow through the channels and/or cavities.

In particular, within the meaning of the present invention, a cartridge is designed to be at least substantially planar and/or card-like, in particular is designed as a (micro)fluidic card and/or is designed as a main body or container that can preferably be closed and/or said cartridge can be inserted and/or plugged into a proposed analysis device when it contains the sample.

The term "assay" is preferably understood to mean an in particular molecular-biological test for detecting or identifying at least one analyte in a sample. In particular, at least one analyte in a sample can be qualitatively and/or quantitatively detected or identified by means of an assay or by carrying out an assay. A plurality of method steps are preferably required to (fully) carry out an assay. Preferably, within the meaning of the present invention, when carrying out an assay, a sample is pretreated with one or more reagents and the pretreated sample is tested, in particular at least one analyte in the sample being detected or identified.

An assay within the meaning of the present invention is in particular an immunoassay and/or protein assay for detecting a target hormone and/or target protein, in particular a target antigen and/or target antibody, particularly preferably by bonding to corresponding capture proteins, a nucleic-acid assay for detecting a target nucleic-acid sequence, in particular a target DNA sequence and/or target RNA sequence, particularly preferably by bonding to corresponding capture nucleic-acid sequences, and/or an aptamer assay for detecting a target protein and/or other target analytes, particularly preferably by bonding to corresponding capture aptamers.

The assays thus differ in particular in terms of the capture molecules used.

In the protein assay, preferably capture proteins are used as the capture molecules, in particular in order for it to be possible to bond and/or detect or identify target analytes corresponding to the capture proteins. In the nucleic-acid assay, preferably capture nucleic-acid sequences are used as the capture molecules, in particular in order for it to be possible to bond and/or detect or identify target analytes corresponding to the capture nucleic-acid sequences. In the aptamer assay, preferably capture aptamers are used as the capture molecules, in particular in order for it to be possible to bond and/or detect or identify target analytes corresponding to the capture aptamers.

The above-mentioned aspects and features of the present invention and the aspects and features of the present invention that will become apparent from the claims and the following description can in principle be implemented independently from one another, but also in any combination or order.

Other aspects, advantages, features and properties of the present invention will become apparent from the following description of a preferred embodiment with reference to the accompanying drawings.

DETAILED DESCRIPTION OF THE INVENTION

In the figures, which are only schematic and sometimes not to scale, the same reference signs are used for the same or similar parts and components, corresponding or comparable properties and advantages being achieved even if these are not repeatedly described.

Figure 1:
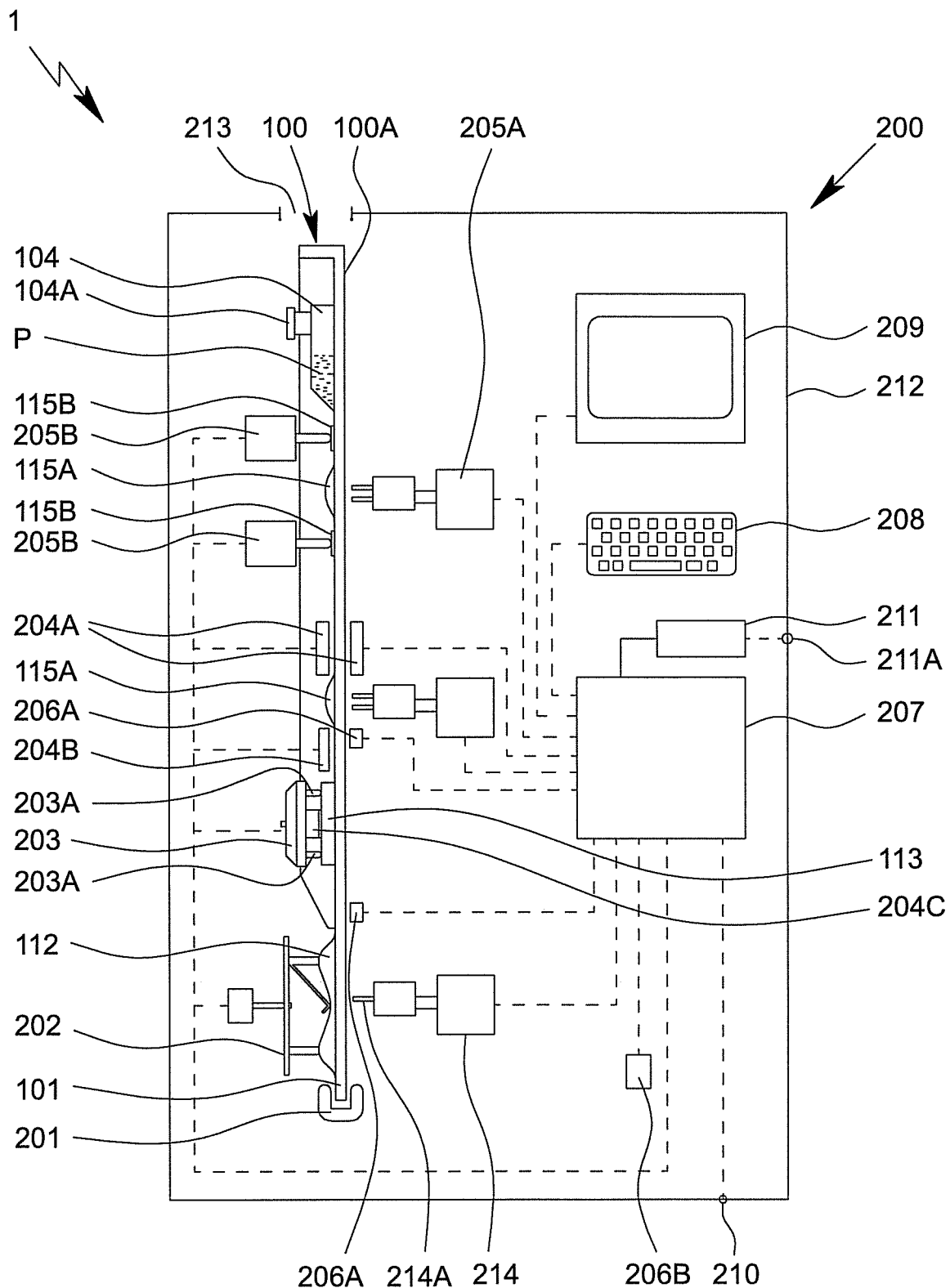
FIG. 1 is a schematic view of a proposed analysis system comprising a proposed analysis device and a proposed cartridge received in the analysis device.

FIG. 1 is a highly schematic view of a proposed analysis system 1 and analysis device 200 for testing, in particular, a biological sample P, preferably by means of or in an apparatus or cartridge 100.

Figure 2:
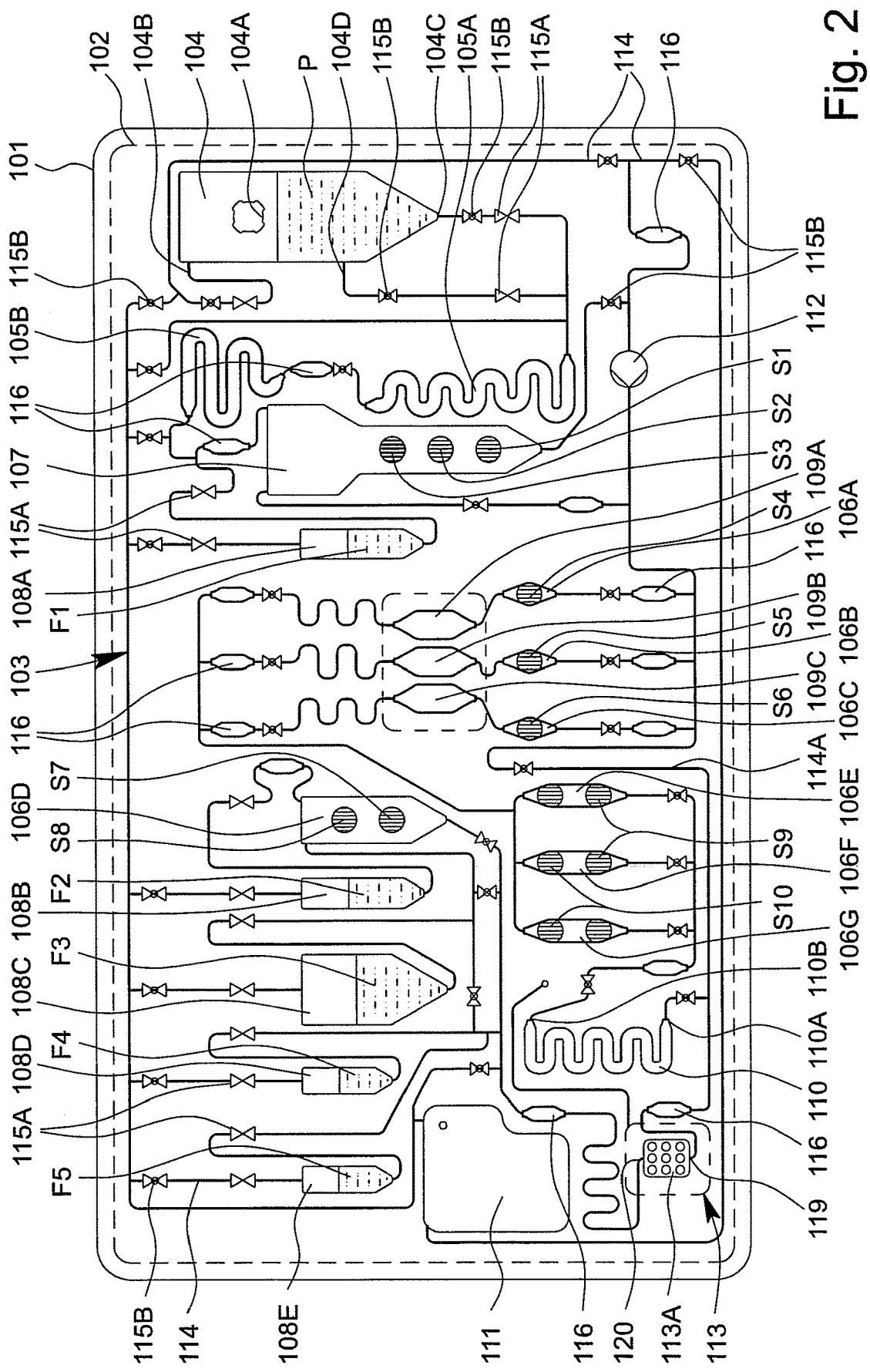
FIG. 2 is a schematic view of the cartridge.

FIG. 2 is a schematic view of a preferred embodiment of the proposed apparatus or cartridge 100 for testing the sample P. The apparatus or cartridge 100 in particular forms a handheld unit, and in the following is merely referred to as a cartridge 100.

The term "sample" is preferably understood to mean the sample material to be tested, which is in particular taken from a human or animal. In particular, within the meaning of the present invention, a sample is a fluid, such as saliva, blood, urine or another liquid, preferably from a human or animal, or a component thereof. Within the meaning of the present invention, a sample may be pretreated or prepared if necessary, or may come directly from a human or animal or the like, for example. A food sample, environmental sample or another sample may optionally also be tested, in particular for environmental analytics, food safety and/or for detecting other substances, preferably natural substances, but also biological or chemical warfare agents, poisons or the like.

A sample within the meaning of the present invention preferably contains one or more analytes, it preferably being possible for the analytes to be identified or detected, in particular qualitatively and/or quantitatively determined. Particularly preferably, within the meaning of the present invention, a sample has target nucleic-acid sequences as the analytes, in particular target DNA sequences and/or target RNA sequences, target proteins as the analytes, in particular target antigens and/or target antibodies, and/or other target analytes, such as hormones, low-molecular substances, steroids, organophosphates, etc. Particularly preferably, at least one disease, pathogen and/or other substances can be detected or identified in the sample P by qualitatively and/or quantitatively determining the analytes.

Preferably, the analysis system 1 or analysis device 200 controls the testing of the sample P in particular in or on the cartridge 100 and/or is used to evaluate the testing or the collection, processing and/or storage of measured values from the test.

By means of the proposed analysis system 1, analysis device 200, and/or the cartridge 100 and/or using the proposed method for testing the sample P, preferably an analyte of the sample P, in particular a (certain) nucleic-acid sequence or target nucleic-acid sequence ZN (see FIG. 9), a (certain) protein or target protein ZP (see FIG. 6/7), and/or another target analyte, can be determined, identified or detected. Particularly preferably, a plurality of analytes of the sample P, in particular a plurality of different target nucleic-acid sequences ZN, different target proteins ZP and/or different other target analytes, can be determined, identified or detected, in particular on a cartridge 100 and/or in two detection steps and/or assays. Said analytes are in particular detected, identified and/or measured not only qualitatively, but, alternatively or additionally, particularly preferably also quantitatively.

Therefore, the sample P can in particular be tested for qualitatively and/or quantitatively determining at least one analyte, for example in order for it to be possible to detect or identify a disease and/or pathogen or to determine other values or substances, which are important for diagnostics, for example.

Particularly preferably, a molecular-biological test is made possible by means of the analysis system 1 and/or analysis device 200 and/or by means of the cartridge 100.

Particularly preferably, a nucleic-acid assay for detecting or identifying a target nucleic-acid sequence ZN, in particular a target DNA sequence and/or target RNA sequence, a protein assay for detecting or identifying a target protein ZP, in particular a target antigen and/or target antibody, and/or an aptamer assay for detecting or identifying a target protein ZP and/or other target analytes, is made possible and/or carried out.

Preferably, the sample P or individual components of the sample P or analytes can be amplified if necessary, in particular by means of PCR, and can be tested, identified and/or detected in the analysis system 1 or analysis device 200 or in the cartridge 100, and/or for the purpose of carrying out the nucleic-acid assay. Preferably, amplification products of the analyte or analytes are thus produced.

In the following, further details are first given on a preferred construction of the cartridge 100, with features of the cartridge 100 preferably also directly representing features of the analysis system 1, in particular even without any further explicit explanation.

The cartridge 100 is preferably at least substantially planar, flat, plate-shaped and/or card-like.

The cartridge 100 preferably comprises an in particular at least substantially planar, flat, plate-shaped and/or card-like main body or support 101, the main body or support 101 in particular being made of and/or injection-moulded from plastics material, particularly preferably polypropylene.

The cartridge 100 preferably comprises at least one film or cover 102 for covering the main body 101 and/or cavities and/or channels formed therein at least in part, in particular on the front, and/or for forming valves or the like, as shown by dashed lines in FIG. 2.

The analysis system 1 or cartridge 100 or the main body 101 thereof, in particular together with the cover 102, preferably forms and/or comprises a fluidic system 103, referred to in the following as the fluid system 103.

The cartridge 100, the main body 101 and/or the fluid system 103 are preferably at least substantially vertically oriented in the operating position and/or during the test, in particular in the analysis device 200, as shown schematically in FIG. 1. In particular, the main plane or surface extension of the cartridge 100 thus extends at least substantially vertically in the operating position.

The cartridge 100 and/or the fluid system 103 preferably comprises a plurality of cavities, in particular at least one receiving cavity 104, at least one metering cavity 105, at least one intermediate cavity 106, at least one mixing cavity 107, at least one storage cavity 108, at least one reaction cavity 109, at least one intermediate temperature-control cavity 110 and/or at least one collection cavity 111, a plurality of cavities preferably being fluidically interconnected in particular by a plurality of channels 114.

Within the meaning of the present invention, channels are preferably elongate forms for conducting a fluid in a main flow direction, the forms preferably being closed transversely, in particular perpendicularly, to the main flow direction and/or longitudinal extension, preferably on all sides.

In particular, the support 101 comprises elongate notches, recesses, depressions or the like, which are closed at the sides by the cover 102 and form channels within the meaning of the present invention.

Within the meaning of the present invention, cavities or chambers are preferably formed by recesses, depressions or the like in the cartridge 100 or support 101, which are closed or covered by the cover 102, in particular at the sides. The space enclosed by each cavity is preferably fluidically linked by means of channels.

In particular, within the meaning of the present invention, a cavity comprises at least two openings for the inflow and/or outflow of fluids.

Within the meaning of the present invention, cavities preferably have a larger diameter and/or flow cross section than channels, preferably by at least a factor of 2, 3 or 4. In principle, however, cavities may in some cases also be elongate, in a similar manner to channels.

The cartridge 100 and/or the fluid system 103 also preferably comprises at least one pump apparatus 112 and/or at least one sensor arrangement or sensor apparatus 113. In particular, the sensor apparatus 113 forms part of a sensor arrangement, as shown in FIGS. 6 to 9.

In the example shown, the cartridge 100 or the fluid system 103 preferably comprises two metering cavities 105A and 105B, a plurality of intermediate cavities 106A to 106G, a plurality of storage cavities 108A to 108E and/or a plurality of reaction cavities 109, which can preferably be loaded separately from one another, in particular a first reaction cavity 109A, a second reaction cavity 109B and an optional third reaction cavity 109C, as can be seen in FIG. 2.

The metering cavities 105 are preferably designed to receive, to temporarily store and/or to meter the sample P, and/or to pass on said sample in a metered manner. Particularly preferably, the metering cavities 105 have a diameter which is larger than that of the (adjacent) channels.

In the initial state of the cartridge 100 or when at the factory, the storage cavities 108 are preferably filled at least in part, in particular with a liquid such as a reagent, solvent or wash buffer.

The collection cavity 111 is preferably designed to receive larger quantities of fluids that are in particular used for the test, such as sample residues or the like. Preferably, in the initial state or when at the factory, the collection cavity 111 is empty or filled with gas, in particular air. The volume of the collection cavity 111 corresponds to or preferably exceeds the (cumulative) volume of the storage cavity/cavities 108 or the liquid content thereof and/or the volume of the receiving cavity 104 or the sample P received.

The reaction cavity/cavities 109 is/are preferably designed to allow a substance located in the reaction cavity 109 to react when an assay is being carried out, for example by being linked or coupled thermally, electrically, mechanically and/or pneumatically to apparatuses or modules of the analysis device 200.

The reaction cavity/cavities 109 is/are used in particular to carry out an amplification reaction, in particular PCR, or several, preferably different, amplification reactions, in particular PCRs. It is preferable to carry out several, preferably different, PCRs, i.e., PCRs having different primer combinations or primer pairs, in parallel and/or separately and/or in different reaction cavities 109.

To carry out the nucleic-acid assay, preferably target nucleic-acid sequences ZN, as analytes of the sample P, are amplified in the reaction cavity/cavities 109 by means of an amplification reaction, in particular in order to produce amplification products for the subsequent detection in the sensor arrangement or sensor apparatus 113.

Within the meaning of the present invention, amplification reactions are in particular molecular-biological reactions in which an analyte, in particular a target nucleic-acid sequence ZN, is amplified/copied and/or in which amplification products, in particular nucleic-acid products, of an analyte are produced. Particularly preferably, PCRs are amplification reactions within the meaning of the present invention.

"PCR" stands for polymerase chain reaction and is a molecular-biological method by means of which certain analytes, in particular portions of RNA or RNA sequences or DNA or DNA sequences, of a sample P are amplified, preferably in several cycles, using polymerases or enzymes, in particular in order to then test and/or detect the amplification products or nucleic-acid products. If RNA is intended to be tested and/or amplified, before the PCR is carried out, a cDNA is produced starting from the RNA, in particular using reverse transcriptase. The cDNA is used as a template for the subsequent PCR.

Preferably, during a PCR, a sample P is first denatured by the addition of heat in order to separate the strands of DNA or cDNA. Preferably, primers or nucleotides are then deposited on the individual separated strands of DNA or cDNA, and a desired DNA or cDNA sequence is replicated by means of polymerase and/or the missing strand is replaced by means of polymerase. This process is preferably repeated in a plurality of cycles until the desired quantity of the DNA or cDNA sequence is available.

For the PCR, marker primers are preferably used, i.e. primers which (additionally) produce a marker or a label L, in particular biotin, on the amplified analyte or analytes or amplification product. This allows or facilitates detection. Preferably, the primers used are biotinylated and/or comprise or form in particular covalently bonded biotin as the label L.

The amplification products, target nucleic-acid sequences ZN and/or other portions of the sample P produced in the one or more reaction cavities 109 can be conducted or fed to the connected sensor arrangement or sensor apparatus 113, in particular by means of the pump apparatus 112.

The sensor arrangement or sensor apparatus 113 is used in particular for detecting, particularly preferably qualitatively and/or quantitatively determining, the analyte or analytes of the sample P, in this case particularly preferably the target nucleic-acid sequences ZN and/or target proteins ZP as the analytes. Alternatively, or additionally, however, other values may also be collected and/or determined.

In particular, the pump apparatus 112 comprises or forms a tube-like or bead-like raised portion, in particular by means of the film or cover 102, particularly preferably on the back of the cartridge 100, as shown schematically in FIG. 1.

The cartridge 100, the main body 101 and/or the fluid system 103 preferably comprise a plurality of channels 114 and/or valves 115, as shown in FIG. 2.

By means of the channels 114 and/or valves 115, the cavities 104 to 111, the pump apparatus 112 and/or the sensor arrangement or sensor apparatus 113 can be temporarily and/or permanently fluidically interconnected and/or fluidically separated from one another, as required and/or optionally or selectively, in particular such that they are controlled by the analysis system 1 or the analysis device 200.

The cavities 104 to 111 are preferably each fluidically linked or interconnected by a plurality of channels 114. Particularly preferably, each cavity is linked or connected by at least two associated channels 114, in order to make it possible for fluid to fill, flow through and/or drain from the respective cavities as required.

The fluid transport or the fluid system 103 is preferably not based on capillary forces, or is not exclusively based on said forces, but in particular is essentially based on the effects of gravity and/or pumping forces and/or compressive forces and/or suction forces that arise, which are particularly preferably generated by the pump or pump apparatus 112. In this case, the flows of fluid or the fluid transport and the metering are controlled by accordingly opening and closing the valves 115 and/or by accordingly operating the pump or pump apparatus 112, in particular by means of a pump drive 202 of the analysis device 200.

Preferably, each of the cavities 104 to 110 has an inlet at the top and an outlet at the bottom in the operating position. Therefore, if required, only liquid from the respective cavities can be removed via the outlet.

In the operating position, the liquids from the respective cavities are preferably removed, in particular drawn out, via the outlet that is at the bottom in each case, it preferably being possible for gas or air to flow and/or be pumped into the respective cavities via the inlet that is in particular at the top. In particular, relevant vacuums in the cavities can thus be prevented or at least minimised when conveying the liquids.

In particular, the cavities, particularly preferably the storage cavity/cavities 108, the mixing cavity 107 and/or the receiving cavity 104, are each dimensioned and/or oriented in the normal operating position such that, when said cavities are filled with liquid, bubbles of gas or air that may potentially form rise upwards in the operating position, such that the liquid collects above the outlet without bubbles. However, other solutions are also possible here.

The receiving cavity 104 preferably comprises a connection 104A for introducing the sample P. In particular, the sample P may for example be introduced into the receiving cavity 104 and/or cartridge 100 via the connection 104A by means of a pipette, syringe or other instrument.

The receiving cavity 104 preferably comprises an inlet 104B, an outlet 104C and an optional intermediate connection 104D, it preferably being possible for the sample P or a portion thereof to be removed and/or conveyed further via the outlet 104C and/or the optional intermediate connection 104D. Gas, air or another fluid can flow in and/or be pumped in via the inlet 104B, as already explained.

Preferably, the sample P or a portion thereof can be removed, optionally and/or depending on the assay to be carried out, via the outlet 104C or the optional intermediate connection 104D of the receiving cavity 104. In particular, a supernatant of the sample P, such as blood plasma or blood serum, can be conducted away, discharged or removed via the optional intermediate connection 104D, in particular for carrying out the protein assay.

Preferably, at least one valve 115 is assigned to each cavity and/or storage cavity 108, the receiving cavity 104, the pump apparatus 112 and/or the sensor apparatus 113 and/or is arranged upstream of the respective inlets and/or downstream of the respective outlets.

Preferably, the cavities 104 to 111 or sequences of cavities 104 to 111, through which fluid flows in series or in succession for example, can be selectively released and/or fluid can selectively flow therethrough by the assigned valves 115 being actuated, and/or said cavities can be fluidically connected to the fluid system 103 and/or to other cavities.

In particular, the valves 115 are formed by the main body 101 and the film or cover 102 and/or are formed therewith and/or are formed in another manner, for example by or having additional layers, depressions or the like.

Particularly preferably, one or more valves 115A are provided which are preferably tightly closed initially or in the storage state, particularly preferably in order to seal liquids or liquid reagents F, located in the storage cavities 108, and/or the fluid system 103 from the open receiving cavity 104 in a storage-stable manner.

Preferably, an initially closed valve 115A is arranged upstream and downstream of each storage cavity 108. Said valves are preferably only opened, in particular automatically, when the cartridge 100 is actually being used and/or during or after inserting the cartridge 100 into the analysis device 200 and/or for carrying out the assay.

A plurality of valves 115A, in particular three valves in this case, are preferably assigned to the receiving cavity 104, in particular if the intermediate connection 104D is provided in addition to the inlet 104B and the outlet 104C. Depending on the use, in addition to the valve 115A on the inlet 104B, then preferably only the valve 115A either at the outlet 104C or at the intermediate connection 104D is opened.

The valves 115A assigned to the receiving cavity 104 seal the fluid system 103 and/or the cartridge 100 in particular fluidically and/or in a gas-tight manner, preferably until the sample P is inserted and/or the receiving cavity 104 or the connection 104A of the receiving cavity 104 is closed.

As an alternative or in addition to the valves 115A (which are initially closed), one or more valves 115B are preferably provided which are not closed in a storage-stable manner and/or which are open initially or in an inoperative position, in an initial state or when the cartridge 100 is not inserted into the analysis device 200, and/or which can be closed by actuation. These valves 115B are used in particular to control the flows of fluid during the test.

The cartridge 100 is preferably designed as a microfluidic card and/or the fluid system 103 is preferably designed as a microfluidic system. In the present invention, the term "microfluidic" is preferably understood to mean that the respective volumes of individual cavities, some of the cavities or all of the cavities 104 to 111 and/or channels 114 are, separately or cumulatively, less than 5 ml or 2 ml, particularly preferably less than 1 ml or 800 μl, in particular less than 600 μl or 300 μl, more particularly preferably less than 200 μl or 100 μl.

Particularly preferably, a sample P having a maximum volume of 5 ml, 2 ml or 1 ml can be introduced into the cartridge 100 and/or the fluid system 103, in particular the receiving cavity 104.

Reagents and liquids which are preferably introduced or provided before the test in liquid form as liquids or liquid reagents F and/or in dry form as dry reagents S are required for testing the sample P, as indicated in the schematic view according to FIG. 2 by reference signs F1 to F5 and S1 to S10.

Furthermore, other liquids F, in particular in the form of a wash buffer, solvent for dry reagents S and/or a substrate SU, for example in order to form detection molecules D and/or a redox system, are also preferably required for the test, the detection process and/or for other purposes, and are in particular provided in the cartridge 100, i.e. are likewise introduced before use, in particular before delivery. At some points in the following, a distinction is not made between liquid reagents and other liquids, and therefore the respective explanations are accordingly also mutually applicable.

The analysis system 1 or the cartridge 100 preferably contains all the reagents and liquids required for pre-treating the sample P and/or for carrying out the test or assay, in particular for carrying out one or more amplification reactions or PCRs, and therefore, particularly preferably, it is only necessary to receive the optionally pre-treated sample P.

The cartridge 100 or the fluid system 103 preferably comprises a bypass 114A that can optionally be used, in order for it to be possible, if necessary, to conduct or convey the sample P or components thereof past the reaction cavities 109 and/or, by bypassing the optional intermediate temperature-control cavity 110, also directly to the sensor apparatus 113.

Preferably, the bypass 114A is used when carrying out the protein assay, in particular in order to feed the sample P or a portion thereof directly from the mixing cavity 107 to the sensor arrangement or sensor apparatus 113, and/or to conduct said sample or portion past the reaction cavities 109 and/or the intermediate temperature-control cavity 110, as explained in greater detail in the following.

The cartridge 100 or the fluid system 103 or the channels 114 preferably comprise sensor portions 116 or other apparatuses for detecting liquid fronts and/or flows of fluid.

It is noted that various components, such as the channels 114, the valves 115, in particular the valves 115A that are initially closed and the valves 115E that are initially open, and the sensor portions 116 in FIG. 2 are, for reasons of clarity, only labelled in some cases, but the same symbols are used in FIG. 2 for each of these components.

The collection cavity 111 is preferably used for receiving excess or used reagents and liquids and volumes of the sample, and/or for providing gas or air in order to empty individual cavities and/or channels. In the initial state, the collection cavity 111 is preferably filled solely with gas, in particular air.

In particular, the collection cavity 111 can optionally be connected to individual cavities and channels or other apparatuses fluidically in order to remove reagents and liquids from said cavities, channels or other apparatuses and/or to replace said reagents and liquids with gas or air. The collection cavity 111 is preferably given appropriate (large) dimensions.

Once the sample P has been introduced into the receiving cavity 104 and the connection 104A has been closed, the cartridge 100 can be inserted into and/or received in the proposed analysis device 200 in order to test the sample P, as shown in FIG. 1. Alternatively, the sample P could also be fed in later.

FIG. 1 shows the analysis system 1 in a ready-to-use state for carrying out a test or assay on the sample P received in the cartridge 100. In this state, the cartridge 100 is therefore linked to, received by and/or inserted into the analysis device 200.

In the following, some features and aspects of the analysis device 200 are first explained in greater detail, in particular on the basis of FIG. 1. The features and aspects relating to said device are preferably also directly features and aspects of the proposed analysis system 1, in particular even without any further explicit explanation.

The analysis system 1 or analysis device 200 preferably comprises a mount or receptacle 201 for mounting and/or receiving the cartridge 100.

Preferably, the cartridge 100 is fluidically, in particular hydraulically, separated or isolated from the analysis device 200. In particular, the cartridge 100 forms a preferably independent and in particular closed or sealed fluidic or hydraulic system 103 for the sample P and the reagents and other liquids. In this way, the analysis device 200 does not come into direct contact with the sample P and can in particular be reused for another test without being disinfected and/or cleaned first.

It is however provided to connect or couple the analysis device 200 mechanically, electrically, thermally and/or pneumatically to the cartridge 100.

In particular, the analysis device 200 is designed to have a mechanical effect, in particular for actuating the pump apparatus 112 and/or the valves 115, and/or to have a thermal effect, in particular for temperature-controlling the reaction cavity/cavities 109 and/or the intermediate temperature-control cavity 110 and/or the sensor apparatus 113.

In addition, the analysis device 200 can preferably be pneumatically connected to the cartridge 100, in particular in order to actuate individual apparatuses, and/or can be electrically connected to the cartridge 100, in particular in order to collect and/or transmit measured values, for example from the sensor apparatus 113 and/or sensor portions 116.

The analysis system 1 or analysis device 200 preferably comprises a pump drive 202, the pump drive 202 in particular being designed for mechanically actuating the pump apparatus 112.

Preferably, a head of the pump drive 202 can be rotated in order to rotationally axially depress the preferably bead-like raised portion of the pump apparatus 112. Particularly preferably, the pump drive 202 and pump apparatus 112 together form a pump, in particular in the manner of a hose pump or peristaltic pump and/or a metering pump, for the fluid system 103 and/or the cartridge 100.

Particularly preferably, the pump is constructed as described in DE 10 2011 015 184 B4. However, other structural solutions are also possible.

Preferably, the capacity and/or discharge rate of the pump can be controlled and/or the conveying direction of the pump and/or pump drive 202 can be switched. Preferably, fluid can thus be pumped forwards or backwards as desired.

The analysis system 1 or analysis device 200 preferably comprises a connection apparatus 203 for in particular electrically and/or thermally connecting the cartridge 100 and/or the sensor arrangement and/or sensor apparatus 113.

As shown in FIG. 1, the connection apparatus 203 preferably comprises a plurality of electrical contact elements 203A, the cartridge 100, in particular the sensor arrangement or sensor apparatus 113, preferably being electrically connected or connectable to the analysis device 200 by the contact elements 203A. The contact elements 203A are preferably contact springs; however, they may also be spring-loaded connection pins or the like.

The analysis system 1 or analysis device 200 preferably comprises one or more temperature-control apparatuses 204 for temperature-controlling the cartridge 100 and/or having a thermal effect on the cartridge, in particular for heating and/or cooling, the temperature-control apparatus(es) 204 (each) preferably comprising or being formed by a heating resistor or a Peltier element.

Individual temperature-control apparatuses 204, some of these apparatuses or all of these apparatuses can preferably be positioned against the cartridge 100, the main body 101, the cover 102, the sensor arrangement, sensor apparatus 113 and/or individual cavities and/or can be thermally coupled thereto and/or can be integrated therein and/or in particular can be operated or controlled electrically by the analysis device 200. In the example shown, in particular the temperature-control apparatuses 204A, 204B and/or 204C are provided.

Preferably, the temperature-control apparatus 204A, referred to in the following as the reaction temperature-control apparatus 204A, is assigned to the reaction cavity 109 or to a plurality of reaction cavities 109, in particular in order for it to be possible to carry out one or more amplification reactions therein.

When the cartridge 100 is inserted, the reaction temperature-control apparatus 204A preferably abuts the cartridge 100 in the region of the reaction cavity/cavities 109, and therefore a fluid located in said cartridge, in particular the sample P, can be heated and/or cooled.

The reaction cavities 109 are preferably temperature-controlled simultaneously and/or uniformly, in particular by means of one common reaction temperature-control apparatus 204A or two reaction temperature-control apparatuses 204A.

Alternatively, each reaction cavity 109 can be temperature-controlled independently and/or individually.

More particularly preferably, the reaction cavity/cavities 109 can be temperature-controlled from two different sides and/or by means of two or the reaction temperature-control apparatus 204A that are preferably arranged on opposite sides.

The temperature-control apparatus 204B, referred to in the following as the intermediate temperature-control apparatus 204B, is preferably assigned to the intermediate temperature-control cavity 110 and/or is designed to (actively) temperature-control or heat the intermediate temperature-control cavity 110 or a fluid located therein, in particular the analytes, amplification products and/or target nucleic-acid sequences ZN, preferably to a preheat temperature, denaturing temperature and/or melting point or melting temperature.

The intermediate temperature-control cavity 110 and/or intermediate temperature-control apparatus 204B is preferably arranged upstream of or (immediately) before the sensor arrangement or sensor apparatus 113, in particular in order for it to be possible to temperature-control or preheat, in a desired manner, fluids to be fed to the sensor arrangement or sensor apparatus 113, in particular analytes, amplification products and/or target nucleic-acid sequences ZN, particularly preferably immediately before said fluids are fed.

Particularly preferably, the intermediate temperature-control cavity 110 or intermediate temperature-control apparatus 204B is designed or intended to denature the sample P, analytes, the amplification products and/or target nucleic-acid sequences ZN produced, and/or to divide and/or melt any double-stranded analytes, amplification products and/or target nucleic-acid sequences ZN into single strands and/or to counteract premature bonding or hybridizing of the amplification products and/or target nucleic-acid sequences ZN, in particular by the addition of heat.

Additionally, or alternatively, the intermediate temperature-control cavity 110 and/or intermediate temperature-control apparatus 204B is designed or provided to thermally activate and/or fold the capture aptamers FA, in particular such that said aptamers FA can bond corresponding target proteins ZP and/or other target analytes, as already explained at the outset.

Preferably, the analysis system 1, analysis device 200 and/or the cartridge 100 and/or one or each temperature-control apparatus 204 comprise/comprises a temperature detector and/or temperature sensor (not shown), in particular in order to make it possible to control and/or feedback control temperature.

One or more temperature sensors may for example be assigned to the sensor portions 116 and/or to individual channel portions or cavities, i.e. may be thermally coupled thereto.

The temperature-control apparatus 204C, referred to in the following as the sensor temperature-control apparatus 204C, is in particular assigned to the sensor apparatus 113 and/or is designed to (actively) temperature-control or heat fluids located in or on the sensor arrangement or sensor apparatus 113, in particular analytes or target proteins ZP or target nucleic-acid sequences ZN, in a desired manner, in particular in order to bond and/or to (then) dissolve or denature said fluids.

Additionally, or alternatively, the sensor temperature-control apparatus 204C is designed or provided to thermally activate and/or fold the capture aptamers FA, in particular such that said aptamers FA can bond corresponding target proteins ZP and/or other target analytes, as already explained at the outset.

The sensor temperature-control apparatus 204C is preferably planar and/or has a contact surface which is preferably rectangular and/or corresponds to the dimensions of the sensor arrangement or sensor apparatus 113, the contact surface allowing for heat transfer between the sensor temperature-control apparatus 204C and the sensor apparatus 113.

Preferably, the analysis device 200 comprises the sensor temperature-control apparatus 204C. However, other structural solutions are also possible in which the sensor temperature-control apparatus 204C is integrated in the cartridge 100, in particular the sensor arrangement or sensor apparatus 113.

Particularly preferably, the connection apparatus 203 comprises the sensor temperature-control apparatus 204C, and/or the connection apparatus 203 together with the sensor temperature-control apparatus 204C can be linked to, in particular pressed against, the cartridge 100, in particular the sensor arrangement or sensor apparatus 113.

More particularly preferably, the connection apparatus 203 and the sensor temperature-control apparatus 204C (together) can be moved towards and/or relative to the cartridge 100, in particular the sensor arrangement or sensor apparatus 113, and/or can be positioned against or abutted on said cartridge, preferably in order to both electrically and thermally couple the analysis device 200 to the cartridge 100, in particular the sensor arrangement or sensor apparatus 113 or the support 113D thereof.

Preferably, the sensor temperature-control apparatus 204C is arranged centrally on the connection apparatus 203 or a support thereof and/or is arranged between the contact elements 203A.

In particular, the contact elements 203A are arranged in an edge region of the connection apparatus 203 or a support thereof or are arranged around the sensor temperature-control apparatus 204C, preferably such that the connection apparatus 203 is connected or connectable to the sensor apparatus 113 thermally in the centre and electrically on the outside or in the edge region. However, other solutions are also possible here.

The analysis system 1 or analysis device 200 preferably comprises one or more actuators 205 for actuating the valves 115. Particularly preferably, different (types or groups of) actuators 205A and 205B are provided which are assigned to the different (types or groups of) valves 115A and 115B for actuating each of said valves, respectively.

The analysis system 1 or analysis device 200 preferably comprises one or more sensors 206. In particular, fluid sensors 206A are assigned to the sensor portions 116 and/or are designed or intended to detect liquid fronts and/or flows of fluid in the fluid system 103.

Particularly preferably, the fluid sensors 206A are designed to measure or detect, in particular in a contact-free manner, for example optically and/or capacitively, a liquid front, flow of fluid and/or the presence, the speed, the mass flow rate/volume flow rate, the temperature and/or another value of a fluid in a channel and/or a cavity, in particular in a respectively assigned sensor portion 116, which is in particular formed by a planar and/or widened channel portion of the fluid system 103.

Particularly preferably, the sensor portions 116 are each oriented and/or incorporated in the fluid system 103 and/or fluid flows against or through the sensor portions 116 such that, in the operating position of the cartridge 100, fluid flows through the sensor portions 116 in the vertical direction and/or from the bottom to the top, or vice versa, in particular in order to make it possible or easier to accurately detect liquid.

Alternatively, or additionally, the analysis device 200 preferably comprises (other or additional) sensors 206B for detecting the ambient temperature, internal temperature, atmospheric humidity, position, and/or alignment, for example by means of a GPS sensor, and/or the orientation and/or inclination of the analysis device 200 and/or the cartridge 100.

The analysis system 1 or analysis device 200 preferably comprises a control apparatus 207, in particular comprising an internal clock or time base for controlling the sequence of a test or assay and/or for collecting, evaluating and/or outputting or providing measured values in particular from the sensor apparatus 113, and/or from test results and/or other data or values.

The control apparatus 207 preferably controls or feedback controls the pump drive 202, the temperature-control apparatuses 204 and/or actuators 205, in particular taking into account or depending on the desired test and/or measured values from the sensor arrangement or sensor apparatus 113 and/or sensors 206.

The flows of fluid are controlled in particular by accordingly activating the pump or pump apparatus 112 and actuating the valves 115.

Particularly preferably, the pump drive 202 comprises a servomotor, stepper motor, or a drive calibrated in another way or a drive having a rotational speed and/or number of (partial) revolutions that can be controlled or feedback controlled, such that desired metering can be achieved, at least in principle, by means of appropriate activation.

Additionally, or alternatively, the fluid sensors 206A are used to detect liquid fronts or flows of fluid, in particular in cooperation with the assigned sensor portions 116, in order to achieve the desired fluidic sequence and the desired metering by accordingly controlling the pump or pump apparatus 112 and accordingly activating the valves 115.

Optionally, the analysis system 1 or analysis device 200 comprises an input apparatus 208, such as a keyboard, a touch screen or the like, and/or a display apparatus 209, such as a screen.

The analysis system 1 or analysis device 200 preferably comprises at least one interface 210, for example for controlling, for communicating and/or for outputting measured data or test results and/or for linking to other devices, such as a printer, an external power supply or the like. This may in particular be a wired or wireless interface 210.

The analysis system 1 or analysis device 200 preferably comprises a power supply 211 for providing electrical power, preferably a battery or an accumulator, which is in particular integrated and/or externally connected or connectable.

Preferably, an integrated accumulator is provided as a power supply 211 and is (re)charged by an external charging device (not shown) via a connection 211A and/or is interchangeable.

The analysis system 1 or analysis device 200 preferably comprises a housing 212, all the components and/or some or all of the apparatuses preferably being integrated in the housing 212. Particularly preferably, the cartridge 100 can be inserted or slid into the housing 212, and/or can be received by the analysis device 200, through an opening 213 which can in particular be closed, such as a slot or the like.

The analysis system 1 or analysis device 200 is preferably portable or mobile. Particularly preferably, the analysis device 200 weighs less than 25 kg or 20 kg, particularly preferably less than 15 kg or 10 kg, in particular less than 9 kg or 6 kg.

As already explained, the analysis device 200 can preferably be pneumatically linked to the cartridge 100, in particular to the sensor arrangement and/or to the pump apparatus 112.

Particularly preferably, the analysis device 200 is designed to supply the cartridge 100, in particular the sensor arrangement and/or the pump apparatus 112, with a working medium, in particular gas or air.

Preferably, the working medium can be compressed and/or pressurised in the analysis device 200 or by means of the analysis device 200.

Preferably, the analysis device 200 comprises a pressurised gas supply 214, in particular a pressure generator or compressor, preferably in order to compress, condense and/or or pressurise the working medium.

The pressurized gas supply 214 is preferably integrated in the analysis device 200 or the housing 212 and/or can be controlled or feedback controlled by means of the control apparatus 207.

Preferably, the pressurized gas supply 214 is electrically operated or can be operated by electrical power. In particular, the pressurized gas supply 214 can be supplied with electrical power by means of the power supply 211.

Preferably, air can be drawn in, in particular from the surroundings, as the working medium by means of the analysis device 200 or pressurized gas supply 214.

The analysis device 200 or pressurized gas supply 214 preferably comprises a connection element 214A, in particular in order to pneumatically connect the analysis device 200 or pressurized gas supply 214 to the cartridge 100.

In the following, further details are given on a preferred construction and the preferred mode of operation of the analysis system 1 and/or the cartridge 100 or the sensor arrangement, with reference to FIG. 3 to FIG. 11. The features of the sensor apparatus 113 and/or of the sensor arrangement formed thereby are preferably also directly features of the analysis system and/or of the cartridge 100, in particular even without any further explicit indication.

The sensor arrangement preferably comprises the sensor apparatus 113, a sensor cover 117 for the sensor apparatus 113, a sensor compartment 118, an inlet 119 into the sensor compartment 118 and/or an outlet 120 out of the sensor compartment 118, as shown in FIG. 2 and FIGS. 6 to 9.

The sensor arrangement, in particular the sensor apparatus 113, is preferably designed for electrochemically measuring or detecting analytes of the sample P.

In particular, the sensor arrangement or sensor apparatus 113 is designed to identify, to detect and/or to determine (identical or different) analytes bonded to capture molecules or products derived therefrom, in particular amplification products of the analyte or different analytes.

The sensor arrangement is preferably designed as a multiple-part module, the sensor apparatus 113 and the sensor cover 117 preferably each forming a component of the sensor arrangement or module.

Preferably, the sensor arrangement has a layered construction, the sensor apparatus 113 preferably forming a base of the sensor arrangement and the sensor cover 117 being directly connected to the sensor apparatus 113, at least at the edge, and/or resting thereon.

The sensor apparatus 113 and the sensor cover 117 define or delimit the sensor compartment 118, preferably on the flat sides. In particular, the sensor compartment 118 is formed or arranged between the sensor apparatus 113 and the sensor cover 117.

The sensor compartment 118 preferably has, in particular when the sensor cover 117 is not actuated or has been moved away, a volume of greater than 0.1 µl or 0.2 µl, particularly preferably greater than 0.5 µl or 1 µl, in particular greater than 2 µl, and/or less than 10 µl or 8 µl, particularly preferably less than 6 µl or 3 µl.

The sensor arrangement, in particular the sensor apparatus 113 and the sensor cover 117, is/are preferably planar, flat and/or plate-shaped. Preferably, the surface area of a flat side of the sensor apparatus 113 and/or sensor cover 117 is less than 400 mm$^2$ or 300 mm$^2$, particularly preferably less than 250 mm$^2$ or 150 mm$^2$, in particular less than 100 mm$^2$ or 50 mm$^2$, and/or greater than 0.01 mm$^2$ or 0.25 mm$^2$, particularly preferably greater than 1 mm$^2$ or 4 mm$^2$.

The sensor apparatus 113 preferably has a front side or measuring side and a rear side or connection side, the measuring side and the connection side each preferably forming one flat side of the in particular flat, planar and/or plate-shaped sensor apparatus 113.

The measuring side is preferably the side of the sensor apparatus 113 facing the fluid or the sample P or the analyte or the sensor compartment 118.

The connection side is preferably opposite the measuring side and/or is the side of the sensor apparatus 113 that faces away from the fluid or the sample P or the analyte or the sensor compartment 118.

The sensor apparatus 113 preferably comprises (precisely) one sensor array 113A on the measuring side, having a plurality of sensor cavities and/or sensor fields 113B, the sensor fields 113B preferably being round, in particular circular, in a plan view of the sensor array 113A and/or being arranged so as to be spatially separated from one another and/or directly next to one another.

Figure 3:
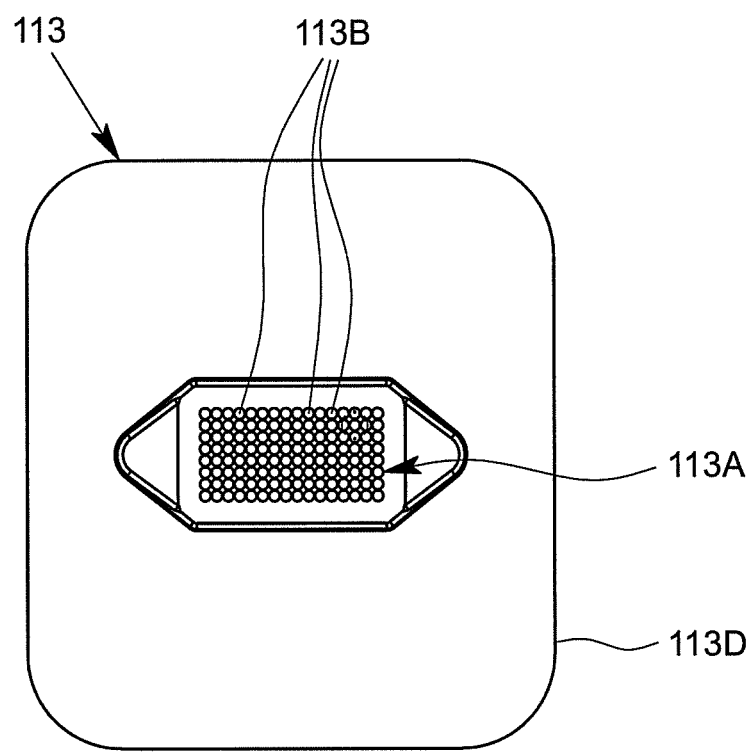
FIG. 3 is a schematic front view of a sensor apparatus of the analysis system and/or cartridge.
Figure 4:
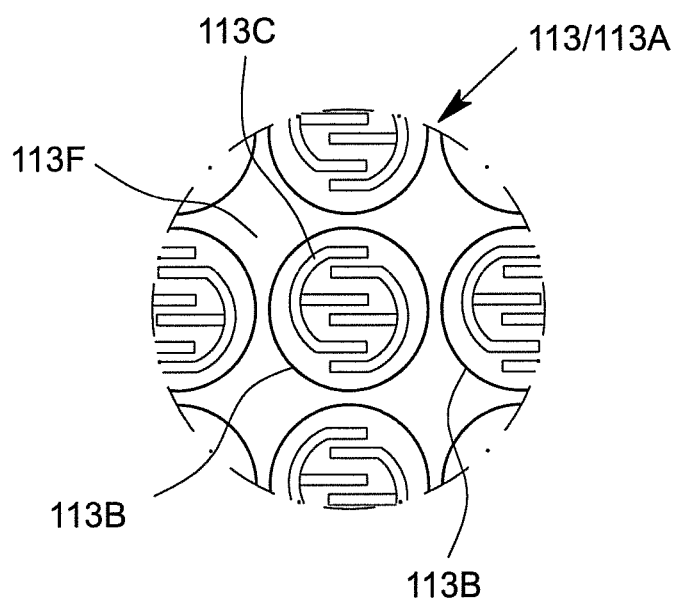
FIG. 4 is an enlarged detail from FIG. 3 illustrating a sensor field of the sensor apparatus.
Figure 5:
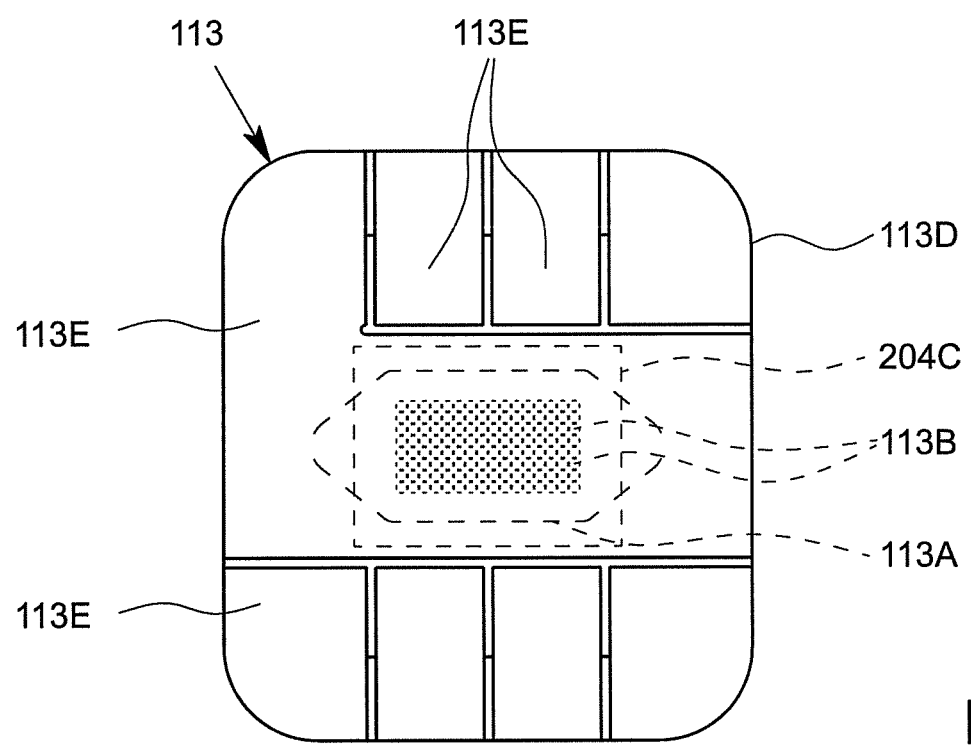
FIG. 5 is a schematic rear view of the sensor apparatus.

FIG. 3 is a plan view of the sensor array 113A or the measuring side of the sensor apparatus 113. FIG. 4 is an enlarged detail from FIG. 3. FIG. 5 shows the connection side of the sensor arrangement or the sensor apparatus 113. FIG. 6 to FIG. 9 are each schematic sections through the sensor arrangement during different method steps.

Preferably, the sensor arrangement or sensor apparatus 113 or the sensor array 113A comprises more than 10 or 20, particularly preferably more than 50 or 80, in particular more than 100 or 120 and/or less than 1000 or 800 sensor fields 113B.

Preferably, the sensor fields 113B are separated or spaced apart from one another, in particular by less than 100 µm or 10 µm and/or more than 10 nm or 100 nm. Particularly preferably, all the sensor fields 113B are arranged on a surface area of less than 100 mm$^2$ and/or greater than 1 mm$^2$ and/or the sensor array 113A has a surface area of less than 100 mm$^2$ and/or greater than 1 mm$^2$.

The sensor fields 113B are in particular spatially separated measuring regions of the sensor apparatus 113 and/or sensor array 113A that, independently from one another, allow an analyte to be detected, identified and/or measured. Different sensor fields 113B can thus detect and/or measure different analytes, respectively. However, a plurality of sensor fields 113B could also measure the same analytes, however, again independently from one another, depending on the capture molecules with which the sensor fields 113 are provided. Alternatively, individual sensor fields 113B can also be used for control purposes, i.e. may not be used for measuring and/or detecting an analyte.

Preferably, the sensor apparatus 113 comprises barriers or partitions between each of the sensor fields 113B, which are preferably formed by an in particular hydrophobic layer 113F having corresponding recesses for the sensor fields 113B. However, other structural solutions are also possible.

Preferably, the sensor arrangement or sensor apparatus 113 or the sensor array 113A comprises a plurality of electrodes 113C. Particularly preferably, at least two electrodes 113C are arranged in each sensor field 113B. In particular, at least or precisely two electrodes 113C corresponding to one another form one or each sensor field 113B.

The electrodes 113C are preferably made of metal, preferably so as to be electrically conductive, in particular at least the surface thereof is made of noble metal, such as platinum or gold.

Preferably, the electrodes 113C are finger-like and/or engage in one another, as can be seen from the enlarged detail of a sensor field 113B according to FIG. 4. However, other structural solutions or arrangements are also possible.

Preferably, each electrode pair forms one sensor field 113B, or each sensor field 113B contains one electrode pair.

The electrodes 113C of a sensor field 113B preferably correspond to one another in terms of their shape and size.

The sensor apparatus 113 preferably comprises a support 113D, in particular a chip comprising an electronic or integrated circuit, and/or a semiconductor chip, the electrodes 113C preferably being arranged on the support 113D and/or being integrated in the support 113D.

The sensor apparatus 113, in particular the support 113D, preferably comprises at least one, preferably a plurality of, electronic or integrated circuits, the circuits in particular being designed to detect electrical currents or voltages that are preferably generated at the sensor fields 113B in accordance with the redox cycling principle.

Particularly preferably, the measurement signals from the different sensor fields 113B are separately collected or measured by the sensor apparatus 113 and/or the circuits.

Particularly preferably, the sensor apparatus 113 and/or the integrated circuits directly convert the measurement signals into digital signals or data, which can in particular be read out by or via the analysis device 200.

Particularly preferably, the sensor apparatus 113 and/or the support 113D is constructed as described in EP 1 636 599 B1.

The sensor apparatus 113, in particular the support 113D, preferably comprises a plurality of, in this case eight, electrical contacts or contact surfaces 113E, the contacts 113E preferably being arranged on the connection side and/or forming the connection side, as shown in FIG. 5.

Preferably, the sensor apparatus 113 can be electrically contacted on the connection side and/or by means of the contacts 113E and/or can be electrically connected to the analysis device 200. In particular, an electrical connection can be established between the cartridge 100, in particular the sensor apparatus 113, and the analysis device 200, in particular the control apparatus 207, by electrically connecting the contacts 113E to the contact elements 203A of the connection apparatus 203.

Preferably, the contacts 113E are arranged laterally, in the edge region and/or in a plan view or projection around the electrodes 113C and/or the sensor array 113A, and/or the contacts 113E extend as far as the edge region of the sensor apparatus 113, in particular such that the sensor apparatus 113 can be electrically contacted, preferably by means of the connection apparatus 203 or the contact elements 203A, laterally, in the edge region and/or around the sensor temperature-control apparatus 204C, which can preferably be positioned centrally or in the middle on the support 113D, as already explained.

As already explained, the sensor compartment 118 is preferably arranged between the sensor apparatus 113 and the sensor cover 117, the measurement side and/or the sensor array 113A of the sensor apparatus 113 preferably defining or delimiting the sensor compartment 118.

Preferably, the sensor fields 113B and/or the electrodes 113C are fluidically interconnected by the sensor compartment 118, in particular such that the sensor fields 113B and/or electrodes 113C can come into contact with a fluid, the sample P and/or the analytes via the (common) sensor compartment 118.

The sensor cover 117 can preferably be moved relative to the sensor apparatus 113. In particular, the sensor cover 117 can be lowered onto the sensor apparatus 113, in particular the sensor array 113A and/or the layer 113F, preferably such that the sensor fields 113B are closed and/or fluidically separated from one another.

In particular, the fluid can be displaced out of the sensor compartment 118 by means of the sensor cover 117, and/or by lowering the sensor cover 117 onto the sensor apparatus 113.

The sensor cover 117 is therefore designed to seal and/or fluidically separate the individual sensor fields 113B from one another for the actual measurement, preferably such that fluid cannot be exchanged (in a relevant manner) between the sensor fields 113B, at least when the measurement is being taken.

Figure 6:
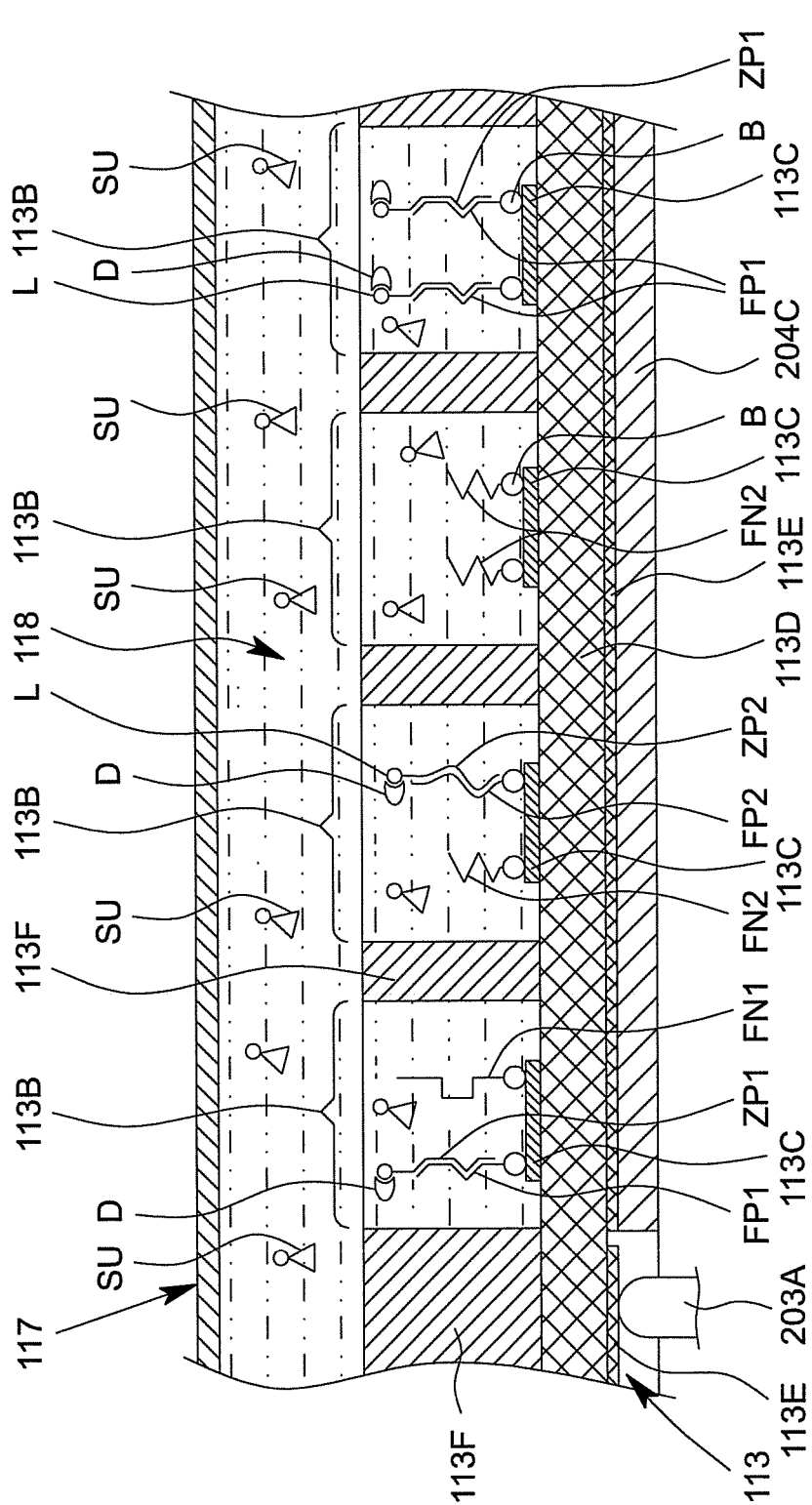
FIG. 6 is a schematic sectional view of a sensor arrangement of the analysis system and/or cartridge comprising the sensor apparatus and a sensor cover that has been moved away.
Figure 7:
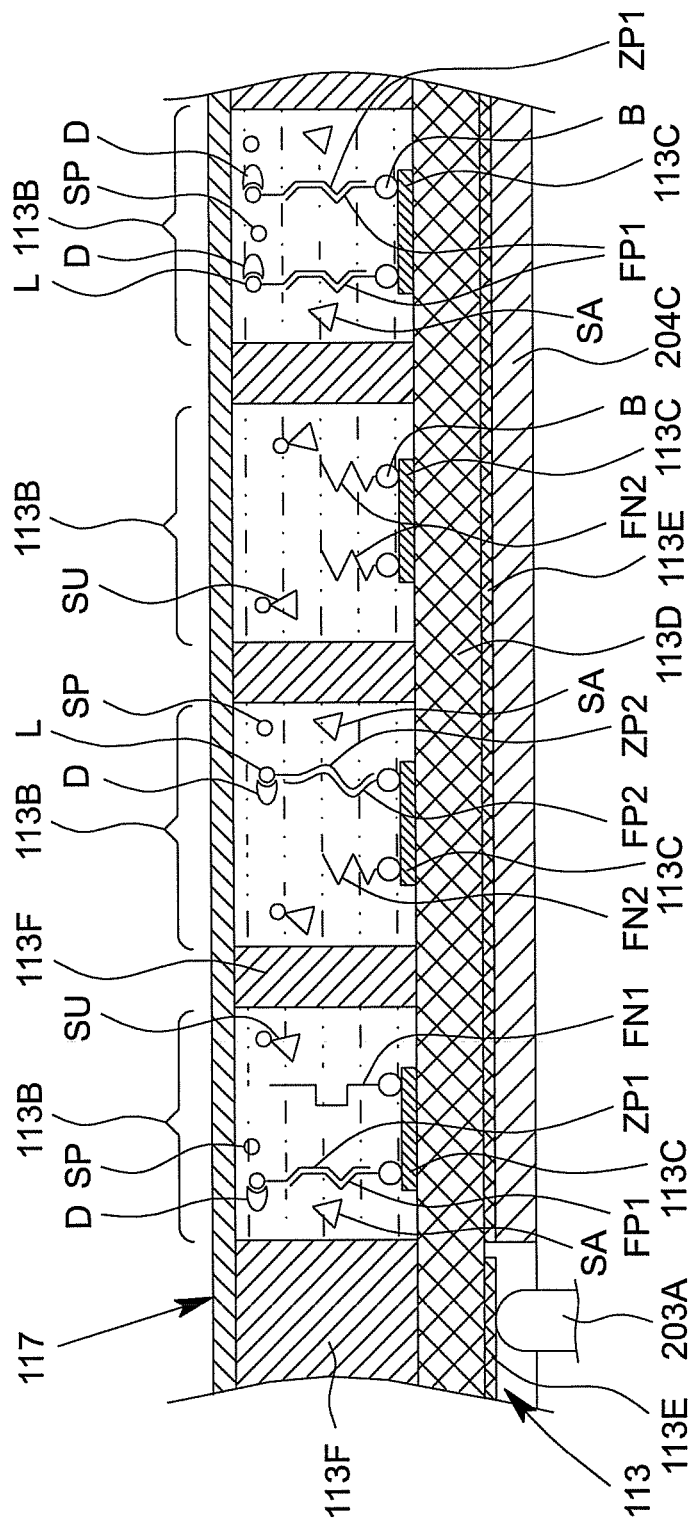
FIG. 7 is a schematic sectional view of the sensor arrangement according to FIG. 6, with the sensor cover lowered.

FIG. 6 is a schematic section through the sensor arrangement with the sensor cover 117 moved away and/or immediately before the measurement. FIG. 7 is a schematic section through the sensor arrangement with the sensor cover 117 lowered onto the layer 113F and/or during the measurement.

At least when the sensor cover 117 is moved away, the sensor apparatus 113 or the sensor compartment 118 is fluidically linked to the fluid system 103, in particular to the reaction cavity/cavities 109, preferably by the inlet 119 and the outlet 120, in particular such that fluids, in particular the (pre-treated) sample P or the analytes and/or reagents, can be admitted to the measurement side of the sensor apparatus 113 or sensor array 113A.

The sensor compartment 118 can thus be loaded with fluids and/or said fluids can flow therethrough, at least when the sensor cover 117 is raised or moved away from the sensor apparatus 113 or the sensor array 113A.

Preferably, fluid can flow through the sensor compartment 118 by means of the inlet 119 and the outlet 120. In particular, a fluid can flow into the sensor compartment 118 via the inlet 119 and can flow out of the sensor compartment 118 via the outlet 120; However, the flow direction can also be reversed. In particular, the inlet 119 can function or be used as the outlet, at least temporarily, and the outlet 120 can function or be used as the inlet, at least temporarily.

The inlet 119 and/or the outlet 120 is/are preferably formed by cut-outs, holes, openings, channels or the like in the main body 101, the sensor cover 117 and/or the sensor apparatus 113.

The sensor apparatus 113 preferably comprises a plurality of in particular different capture molecules for bonding the analytes, different capture molecules preferably being arranged and/or immobilized in or on different sensor fields 113B and/or being assigned to different sensor fields 113B.

Particularly preferably, the sensor fields 113B or electrodes 113C are provided with the capture molecules, in particular at the factory, and/or the capture molecules are immobilized or fixed in or on the sensor fields 113B or electrodes 113C, in particular at the factory.

Figure 12:
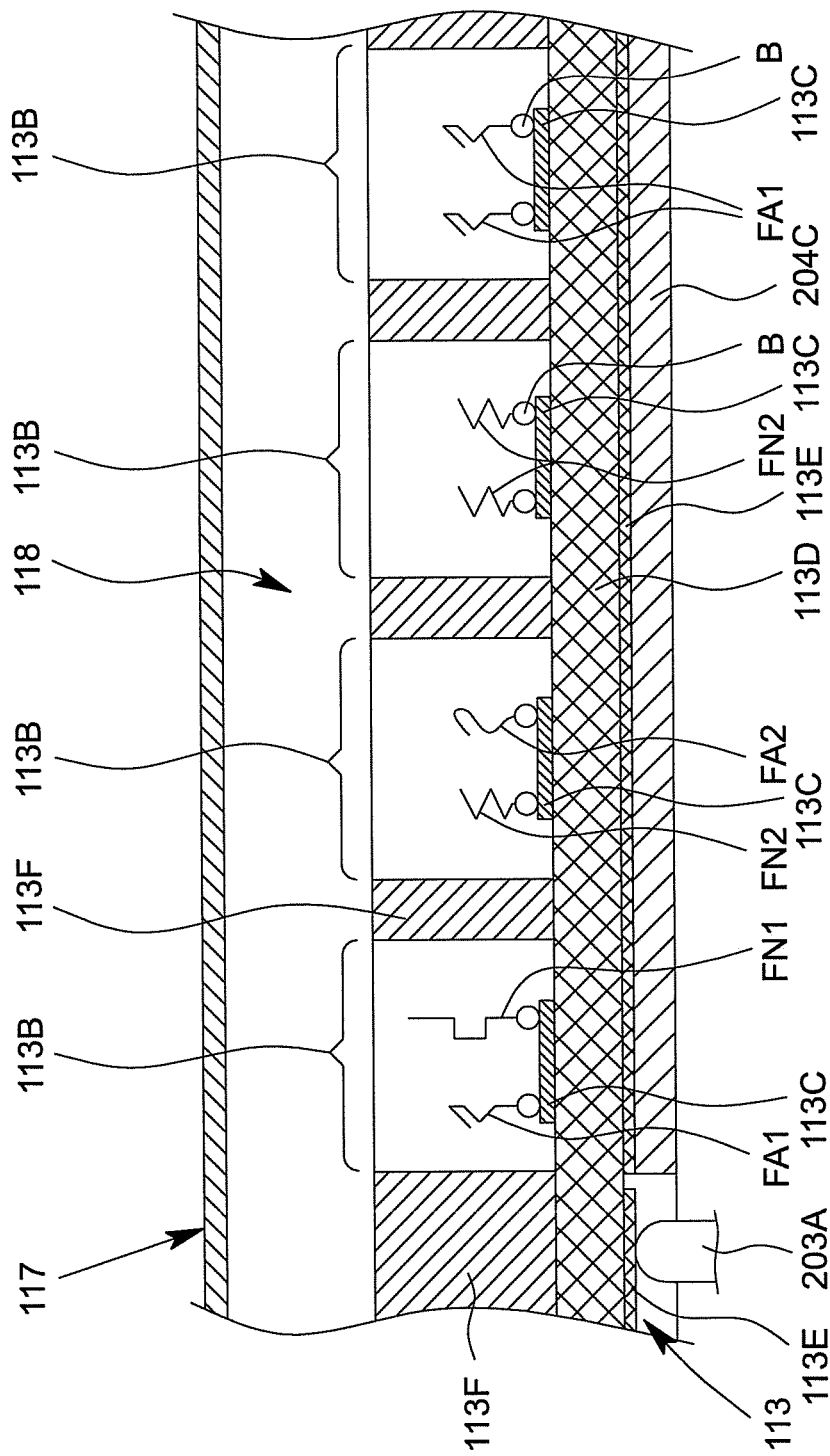
FIG. 12 is a schematic sectional view, corresponding to FIG. 6, of the sensor arrangement comprising different capture molecules.

As already explained at the outset, the capture molecules are preferably capture proteins FP, in particular capture antigens and/or capture antibodies, capture nucleic-acid sequences FN, in particular capture DNA sequences and/or capture RNA sequences, oligonucleotides or fragments of PCR products, and/or, in particular additionally or alternatively to the capture proteins FP, capture aptamers FA (shown only in FIG. 12).

Preferably, the cartridge 100 and/or the sensor apparatus 113 comprises a first group of capture molecules, such as capture proteins FP or capture aptamers FA, for bonding a first type of target molecules and/or analytes, and in particular a second group of (different) capture molecules, such as capture nucleic-acid sequences FN, for bonding another type of target molecules and/or analytes. Particularly preferably, the first group of capture molecules, in particular in contrast to the second group of capture molecules, can either be thermally blocked, deactivated and/or denatured, preferably by heating, such as capture proteins FP, or thermally activated, such as capture aptamers FA, such that in particular two different assays can be carried out, in particular in succession and/or on the same cartridge 100 and/or sensor apparatus 113, using the two groups of capture molecules.

Preferably, the cartridge 100 and/or sensor apparatus 113 comprises both capture nucleic-acid sequences FN (FN1, FN2) and capture proteins FP (FP1, FP2) as capture molecules, as shown in FIG. 6. In an alternative embodiment, the cartridge 100 and/or sensor apparatus 113 comprises both capture nucleic-acid sequences FN and, in particular as an alternative to the capture proteins FP, capture aptamers FA as capture molecules, as explained in greater detail in the following with reference to FIG. 12. Furthermore, embodiments are also possible in which the cartridge 100 and/or sensor apparatus 113 comprises both capture proteins FP and capture aptamers FA as capture molecules, the capture aptamers FA preferably being designed, in this case, to bond different target analytes from the capture proteins FP and/or to bond target analytes that are different than the target proteins ZP, such as other low-molecular substances, steroids, organophosphates, or the like.

As shown in FIG. 6, preferably some or all of the sensor fields 113B and/or electrodes 113C are provided, respectively, with both capture proteins FP and capture nucleic-acid sequences FN, in particular in order to be able to detect or identify the target proteins ZP that correspond to the capture proteins FP and target nucleic-acid sequences ZN that correspond to the capture nucleic-acid sequences FN by means of the sensor apparatus 113 and/or in the corresponding sensor fields 113B and/or on the corresponding electrodes 113C.

In other words, preferably both capture proteins FP and capture nucleic-acid sequences FN are applied to, fixed to and/or immobilised on a common sensor field 113B and/or a common electrode 113C and/or are applied, fixed and/or immobilised directly next to one another, as shown in FIG. 6 and FIG. 7 for the first and second sensor field 113B (from the left).

Figure 9:
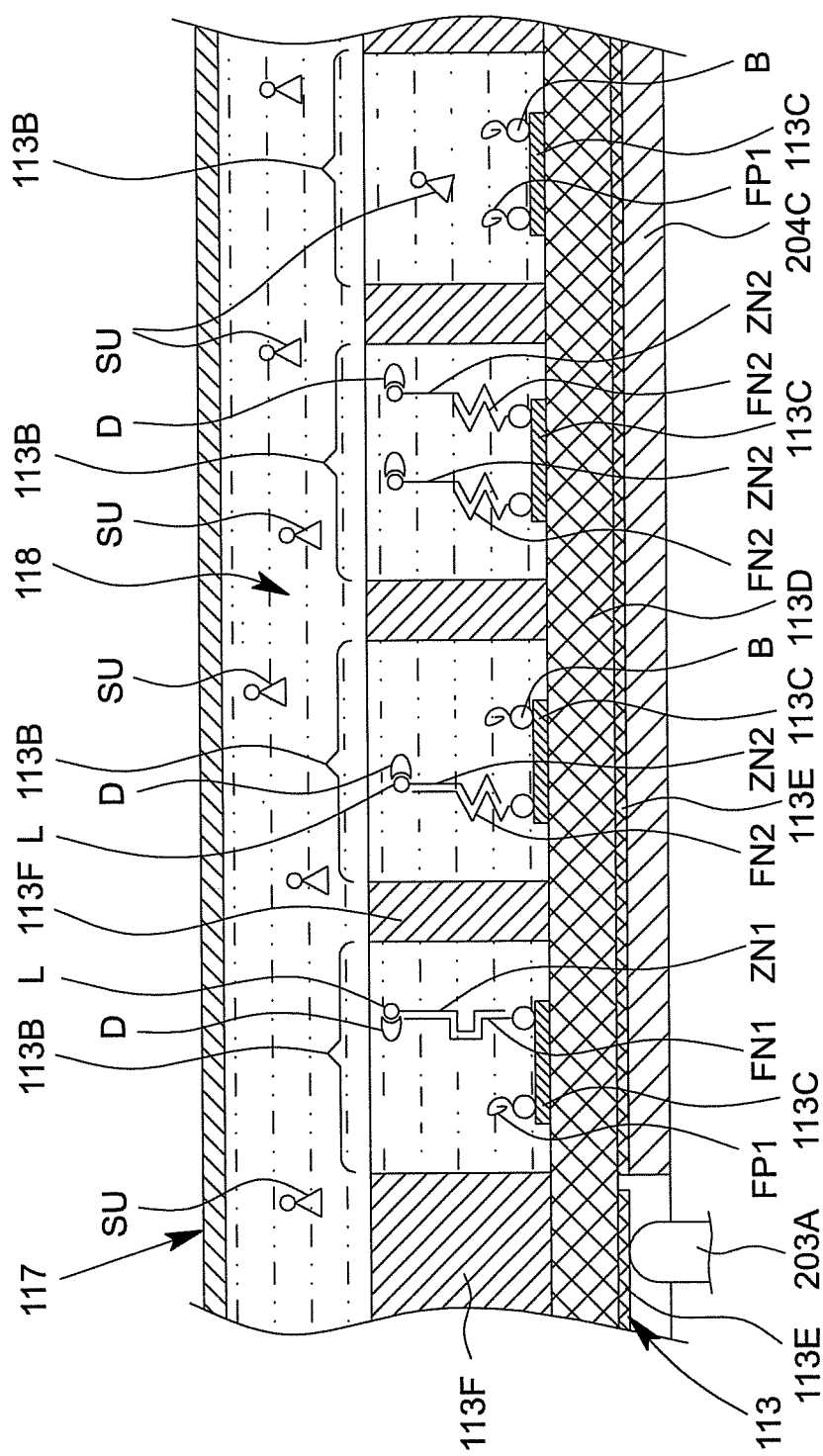
FIG. 9 is a schematic sectional view of the sensor arrangement while a nucleic-acid assay is being carried out.

Preferably, one sensor field 113B is thus used not just for detecting one analyte, but rather for detecting and in particular measuring at least two analytes, specifically a target protein ZP on the one hand (in FIG. 6, e.g., ZP1 and/or ZP2) and a target nucleic-acid sequence ZN on the other hand (in FIG. 9 e.g. ZN1 and/or ZN2). The corresponding capture molecules, specifically capture proteins FP and capture nucleic-acid sequences FN, can in this case be arranged and/or immobilized together on each of the electrodes 113C of the sensor field 113B or, at least in theory, separately on the two electrodes 113C of the same sensor field 113B.

It is thus possible to carry out twice the number of detection processes and/or measurements of analytes using the same number of sensor fields 113B.

Additionally, or alternatively, it is possible for either only capture proteins FP or only capture nucleic-acid sequences FN to be fixed and/or immobilized in some or all of the sensor fields 113B, as shown by way of example in FIG. 6 to FIG. 9 for the third and fourth sensor field 113B (from the left). For example, only capture nucleic-acid sequences FN2 are provided and/or immobilized in the third sensor field 113B, while only capture proteins FP1 are provided and/or immobilized in the fourth sensor field 113B.

It is proposed for the analysis system 1, the cartridge 100, the sensor apparatus 113 and/or the sensor array 113A to comprise both capture proteins FP and capture nucleic-acid sequences FN, which are provided and/or immobilized together or separately in sensor fields 113B.

It is thus possible and provided for both a protein assay for detecting a target protein ZP, in particular a plurality of different target proteins ZP, and a nucleic-acid assay for detecting a nucleic-acid sequence ZN, in particular a plurality of different nucleic-acid sequences ZN, to be carried out using the analysis system 1 and/or by means of the cartridge 100 and/or sensor apparatus 113, in particular in and/or by means of the same cartridge 100.

Different capture proteins FP1 and/or FP2 and/or different capture nucleic-acid sequences FN1 and/or FN2 are preferably provided for the different sensor fields 113B and/or the different electrode pairs and/or electrodes 113C, in order to specifically bond different analytes, in particular different target proteins ZP1, ZP2 on the one hand and different target nucleic-acid sequences ZN1, ZN2 on the other hand, in the sensor fields 113B.

Particularly preferably, the sensor apparatus 113 or sensor array 113A allows the analytes bonded in each sensor field 113B to be qualitatively and/or quantitatively determined.

Preferably, the capture molecules are bonded to the sensor apparatus 113, the sensor array 113A and/or the electrodes 113C by a bond B, in particular a thiol bond, and/or, optionally, by a so-called spacer, in particular a C6 spacer. The formation of structures that disrupt hybridization, e.g., hairpin structures, can be prevented by the preferred bonding of the capture molecules by the bond B.

Optionally, the sensor apparatus 113 comprises capture molecules having different hybridization temperatures, preferably in order to bond the analytes to the corresponding capture molecules at different hybridization temperatures.

The hybridization temperature is preferably the (average) temperature at which an (amplified) analyte or a target nucleic-acid sequence ZN or a target protein ZP is bonded to a corresponding capture molecule or a corresponding capture nucleic-acid sequence FN or a corresponding capture protein FP.

The optimal hybridization temperature is preferably the temperature at which the number of analytes bonded to corresponding capture molecules is maximized and/or the number of analytes bonded to one another is minimized.

Preferably, the (optimal) hybridization temperature varies for different analytes, in particular target nucleic-acid sequences ZN.

Preferably, the hybridization temperature for bonding the target nucleic-acid sequences ZN to the capture nucleic-acid sequences FN is (significantly) higher than the hybridization temperature for bonding the target proteins ZP to the capture proteins FP, particularly preferably by more than 10° C. or 15° C.

Preferably, the denaturing temperature of the capture proteins FP and/or target proteins ZP is significantly lower than the denaturing temperature and/or melting point or melting temperature of the capture nucleic-acid sequences FN and/or target nucleic-acid sequences ZN, particularly preferably by more than 20° C. or 30° C.

The denaturing temperature of the capture proteins FP and/or target proteins ZP is preferably the (average) temperature at and/or from which the capture proteins FP and/or target proteins ZP are degraded or a spatial structure thereof is destroyed, and/or at and/or from which the bond between target proteins ZP and capture proteins FP is broken and/or destroyed.

The denaturing temperature of the capture proteins FP and/or target proteins ZP is preferably greater than 30° C. or 40° C., in particular greater than 45° C. or 50° C., and/or less than 90° C. or 80° C., in particular less than 70° C.

The denaturing temperature and/or melting point of the capture nucleic-acid sequences FN and/or target nucleic-acid sequences ZN is preferably the (average) temperature at and/or from which the bond between the target nucleic-acid sequences ZN and the capture nucleic-acid sequences FN is broken, i.e., when the sequences are separated.

Preferably, the denaturing temperature and/or melting point or melting temperature of the capture nucleic-acid sequences FN and/or target nucleic-acid sequences ZN is greater than 80° C. or 90° C., in particular greater than 95° C. or 100° C., and/or less than 120° C. or 110° C.

Particularly preferably, the analysis system 1 and/or the cartridge 100 is designed such that first a protein assay and then a nucleic-acid assay can be carried out.

During the protein assay, the analytes and/or target proteins ZP are bonded to the capture proteins FP and then detection and/or measurement is carried out. During the nucleic-acid assay, the analytes and/or target nucleic-acid sequences ZN are bonded to the capture nucleic-acid sequences FN and then detection and/or measurement is carried out.

Preferably, the capture proteins FP and/or target proteins ZP are denatured, in particular by a corresponding effect of heat, or degraded or blocked in another manner, after the protein assay has been carried out.

The analysis system 1 and/or analysis device 200 and/or the cartridge 100 is/are preferably designed such that a corresponding effect of temperature or heating for denaturing the capture proteins FP and/or target proteins ZP is made possible and in particular ensured. According to a variant, the capture proteins FP and/or target proteins ZP can be denatured by conducting or by the effect of a fluid that is heated to above the denaturing temperature of the capture protein FP. This fluid that is preferably heated by means of the intermediate temperature-control apparatus 204B can be a washing solution, a buffer, nucleic-acid sequences and/or target nucleic-acid sequences ZN, and/or in particular amplification products produced by PCR.

According to a particularly preferred variant of the method, it is possible to denature the capture proteins FP (including target proteins ZP bonded thereto) after the protein assay by conducting and/or feeding correspondingly heated target nucleic-acid sequences ZN for the nucleic-acid assay.

Preferably, the temperature of the sensor apparatus 113, in particular of the electrodes 113C, the support 113D, the sensor compartment 118 and/or the sensor cover 117, can be controlled or set, at least indirectly, preferably by means of the analysis device 200, in particular by means of the temperature-control apparatus(es) 204B and/or 204C, as already explained. It is thus possible in particular for the capture proteins FP and/or target proteins ZP to be acted on for the purpose of denaturing.

Preferably, the sensor temperature-control apparatus 204C is used to temperature-control the sensor compartment 118, in this case by being in contact with the connection side of the sensor apparatus 113, in particular such that the desired or required or optimal denaturing temperature and/or hybridization temperature is set on the measuring side and/or in the sensor compartment 118.

Optionally, it is possible to denature hybridized target proteins ZP and capture proteins FP and/or to break the bond between the target proteins ZP and capture proteins FP by means of the sensor temperature-control apparatus 204C and/or by temperature-controlling the sensor compartment 118, after the protein assay has been carried out and/or before the start of the nucleic-acid assay. In this way, a possible disruptive effect that target proteins ZP bonded to capture proteins FP may have on the measurement of target nucleic-acid sequences ZN bonded to capture nucleic-acid sequences FN can be prevented or at least reduced.

In the following, a preferred sequence of a test or analysis using the proposed analysis system 1 and/or analysis device 200 and/or the proposed cartridge 100 and/or in accordance with the proposed method is explained in greater detail by way of example.

The analysis system 1, the cartridge 100 and/or the analysis device 200 is preferably designed to carry out the proposed method.

The method may be used in particular in the field of medicine, in particular veterinary medicine, for example in order to detect or identify diseases and/or pathogens. Alternatively, the method may also be used for other purposes, for example for food safety, environmental analytics or the like.

In the proposed method, a plurality of (different) assays for detecting or identifying (different) target analytes of the sample P are carried out, in particular sequentially and/or in the same cartridge 100 and/or sensor apparatus 113. Preferably, at least or precisely two (different) assays are carried out from the selection group consisting of a protein assay, a nucleic-acid assay and/or an aptamer assay.

Preferably, a protein assay is carried out in order to detect or identify a target protein ZP, in particular a target antigen and/or target antibody. In particular, target proteins ZP are bonded to corresponding capture molecules, in particular capture proteins FP, in the form of analytes of the sample P.

Preferably, a nucleic-acid assay is carried out, in particular in addition to the protein assay, in order to detect or identify a target nucleic-acid sequence ZN, in particular a target DNA sequence and/or target RNA sequence. Particularly preferably, target nucleic-acid sequences ZN are bonded to corresponding capture molecules, in particular capture nucleic-acid sequences FN, in the form of analytes of the sample P.

Optionally, an aptamer assay is carried out, in particular as an alternative to the protein assay, in order to detect or identify a target protein ZP or another target analyte that is different from the target protein ZP. As already explained, the aptamer assay can, however, also be carried out in addition to the protein assay and/or as an alternative to the nucleic-acid assay. In the following, however, a first, particularly preferred variant of the method is described first of all, in which both a protein assay and a nucleic-acid assay are carried out. However, any explanations relating to preparing and/or carrying out the respective assays apply correspondingly to other combinations from the selection group consisting of a protein assay, a nucleic-acid assay and/or an aptamer assay.

During the nucleic-acid assay, at least one analyte of the sample P is preferably amplified or copied, in particular by means of PCR. A method step of this type is preferably omitted when carrying out the protein assay.

Preferably, the bonded analytes or the amplification products thereof are electrochemically identified or detected, in particular both in the protein assay and in the nucleic-acid assay.

In the first variant of the method, the protein assay and the nucleic-acid assay are preferably carried out sequentially, the protein assay preferably being carried out before the nucleic-acid assay. In particular, the target proteins ZP are first bonded to the corresponding capture proteins FP and detected, and only subsequently are the target nucleic-acid sequences ZN bonded to the corresponding capture nucleic-acid sequences FN and detected, as explained in detail in the following.

At the start of the proposed method, a sample P having at least one analyte, preferably a fluid or a liquid from the human or animal body, in particular blood, saliva or urine, is preferably first introduced into the receiving cavity 104 via the connection 104A, it being possible for the sample P to be pretreated, in particular filtered.

In particular, both the protein assay and the nucleic-acid assay are carried out using the same sample P.

Once the sample P has been received, the receiving cavity 104 and/or the connection 104A thereof is fluidically closed, in particular in a liquid-tight and/or gas-tight manner.

Preferably, the cartridge 100 together with the sample P is then linked to the analysis device 200, in particular is inserted or slid into the analysis device 200 or the opening 213, particularly preferably from the top.

Particularly preferably, the cartridge 100 is received, at least substantially vertically, by the analysis device 200.

The method sequence, in particular the flow and conveying of the fluids, the mixing and the like, is controlled by the analysis device 200 or the control apparatus 207, in particular by accordingly activating and actuating the pump drive 202 or the pump apparatus 112 and/or the actuators 205 or valves 115.

Preferably, the sample P or a part or supernatant of the sample P is removed from the receiving cavity 104, in particular via the outlet 104C, preferably for carrying out the nucleic-acid assay, and/or via the intermediate connection 104D, in particular for carrying out the protein assay, and is preferably fed to the mixing cavity 107 in a metered manner.

Particularly preferably, the sample P is split into at least two sample portions, a first sample portion being used for carrying out the protein assay and a second sample portion being used for carrying out the nucleic-acid assay. Preferably, the sample P is split into the different sample portions for the assays by being removed via the outlet 104C and the intermediate connection 104D. Other variants of the method are also possible, however, in particular in which the sample P is split into different sample portions for the assays by being removed sequentially from the mixing cavity 107.

In the following, firstly the method steps required for the protein assay are described, and then the method steps required for the nucleic-acid assay are described.

Preferably, the sample P or a portion thereof is removed for the protein assay, optionally via the outlet 104C or the intermediate connection 104D of the receiving cavity 104.

Preferably, the sample P or a portion thereof for the protein assay in the cartridge 100 is metered, in particular in or by means of the first metering cavity 105A and/or second metering cavity 105B, before being introduced into the mixing cavity 107. Here, in particular the upstream and/or downstream sensor portions 116 are used together with the assigned sensors 206 in order to make possible the desired metering. However, other solutions are also possible.

Preferably, the sample P or a portion thereof for the protein assay is removed from the mixing cavity 107 and fed to the sensor arrangement and/or sensor apparatus 113, preferably directly, in particular via the bypass 114A and/or past the reaction cavities 109.

It is important that the sample P or sample portion for the protein assay should not be heated to or above the denaturing temperature. This should be taken into account while conducting said sample P to the sensor arrangement and/or sensor apparatus 113.

In order to carry out the protein assay, the sample P or sample portion can, if required, be pretreated in the cartridge 100, or can be conducted to the sensor arrangement and/or sensor apparatus 113 without being pretreated. The latter case is possible in particular when, for example, a supernatant of the sample P is discharged via the intermediate connection 114D and conducted to the sensor arrangement or sensor apparatus 113 as a sample portion. However, other method sequences are also possible here. It is also conceivable, for the protein assay, for the sample P or sample portion to be conducted through one or more of the reaction cavities 109, but without the cyclical temperature control necessary for the nucleic-acid assay being carried out therein. It is also possible for the sample P to be conducted through the intermediate temperature-control cavity 110, but without the sample P being heated above the denaturing temperature of the target proteins ZP in the process. In this way, the apparatuses present on the cartridge 100, including the cavities, can be used when carrying out the protein assay, at least for feeding or conducting the sample P to the sensor arrangement and/or sensor apparatus 113 and/or for mixing reagents. Thus, advantageously, at least some of the same channels and/or cavities can be used for a protein assay as can also be used for the nucleic-acid assay, or vice versa.

Preferably, the target proteins ZP of the sample P or sample portion are bonded to the corresponding capture proteins FP and identified or detected, in particular electrochemically and/or by redox cycling, in the sensor arrangement and/or sensor apparatus 113.

Preferably, during hybridisation and/or detection of the target proteins ZP there are preferably no target nucleic-acid sequences ZN in the sensor compartment 118 and/or the sensor fields 113B. In particular, during the protein assay there are no amplification products and/or no single-stranded target nucleic-acid sequences ZN in the sensor compartment 118 that could bond to the corresponding capture nucleic-acid sequences FN and thus influence and possibly distort the detection of the target proteins ZP.

Preferably, the capture nucleic-acid sequences FN remain free and/or unbonded and/or undamaged during hybridisation and/or detection of the target proteins ZP, in particular in order to be able to bond the corresponding target nucleic-acid sequences ZN subsequently and/or after the protein assay has been carried out.

FIG. 6 is a schematic sectional detail of the sensor arrangement when the sensor cover 117 is raised and/or not lowered and while the protein assay is being carried out.

The target proteins ZP1 and ZP2 of the sample P have already bonded to corresponding capture proteins FP1 and FP2.

FIG. 6 further shows the state already after addition of a label L that bonds to the bonded target proteins ZP and/or to the complexes of capture proteins FP and target proteins ZP and thus marks or labels said proteins and/or complexes.

Detector molecules D which contain an enzyme that can react catalytically with the added substrate SU are then bonded to the marker or label L.

FIG. 7 is a schematic sectional view of the sensor arrangement which corresponds to FIG. 6 and in which the sensor cover 117 is lowered. The detector molecules D have already split and/or broken down the provided substrate SU in part into the components SA and SP. Lowering the sensor cover 117 at least largely stops an exchange of substances between the sensor fields 113B.

The electrochemical measurement can now be carried out, in particular by means of what is known as redox cycling.

The electrochemical detection in the protein assay and/or aptamer assay is preferably carried out, at least substantially, in the same way as in the nucleic-acid assay, and will be explained in greater detail subsequently for all the assays together.

After the end of the protein assay and/or detection of the bonded target proteins ZP, the sensor apparatus 113 and/or the sensor compartment 118 is prepared for the subsequent nucleic-acid assay.

Preferably, after the end of the protein assay and/or in order to prepare the nucleic-acid assay, the sensor apparatus 113 and/or the sensor compartment 118 and/or the intermediate temperature-control apparatus 204B is heated, in particular to at least the denaturing temperature of the target proteins ZP and/or capture proteins FP and/or to the temperature required for denaturing target proteins ZP and capture proteins FP that are bonded to one another, preferably by means of the sensor temperature-control apparatus 204C and/or by conducting a fluid that has been correspondingly preheated, preferably by means of the intermediate temperature-control apparatus 204B.

Particularly preferably, the sensor apparatus 113 and/or the sensor compartment 118 is heated and/or brought to or above the denaturing temperature for a time period of more than 1 sec or 2 sec, in particular more than 3 sec or 5 sec, and/or less than 120 sec or 90 sec. This ensures that all or almost all of the target proteins ZP and/or capture proteins FP are denatured.

In particular, after the detection and/or after the protein assay has been carried out, the target proteins ZP bonded to the capture proteins FP are denatured and/or removed from the sensor apparatus 113, in particular the capture proteins FP and/or the electrodes 113C, preferably by the addition of heat, particularly preferably by heating the sensor apparatus 113 and/or the sensor compartment 118, and/or by conducting a fluid heated by the intermediate temperature-control apparatus 204B.

The addition of heat preferably denatures both the target proteins ZP and the capture proteins FP, such that the target proteins ZP are detached from the capture proteins FP. Generally, however, the (denatured) capture proteins FP do not detach from the sensor array 113A and/or from the electrodes 113C due to the addition of heat, but rather remain connected to the electrodes 113C despite the addition of heat. However, this does not result in any influence on the subsequent nucleic-acid assay, since, due to the denaturing thereof, the capture proteins FP are deactivated and/or cannot bond any target proteins ZP and thus cannot impair the measurement during the nucleic-acid assay. Variants of the method are also possible, however, in which both the target proteins ZP and the capture proteins FP detach from the sensor array 113A and/or from the electrodes 113C.

Preferably, the sensor cover 117 remains lowered when the sensor apparatus 113 is heated. This advantageously allows rapid heating of the (closed) sensor fields 113B. Variants of the method are also possible, however, in which the sensor cover 117 is raised from the sensor apparatus 113 prior to or for the purpose of heating the sensor apparatus 113.

Preferably, the sensor apparatus 113 and/or the sensor compartment 118 is and/or the capture proteins FP and target proteins ZP are heated to a temperature of at least 50° C., preferably greater than 70° C., and in particular greater than 90° C., for the purpose of denaturing, the capture nucleic-acid sequences FN and/or (any) target nucleic-acid sequences ZN remaining undamaged or intact and/or not denaturing, and/or being available for the subsequent nucleic-acid assay.

Preferably, a washing and/or flushing process of the sensor arrangement, in particular the sensor compartment 118 and/or the sensor fields 113B, takes place after the denaturing, preferably by means of the fluid or reagent F3 or wash buffer, in particular in order to remove the denatured and/or detached capture proteins FP and/or target proteins ZP or remnants thereof from the sensor arrangement and/or the sensor compartment 118 and/or the sensor fields 113B.

Figure 8:
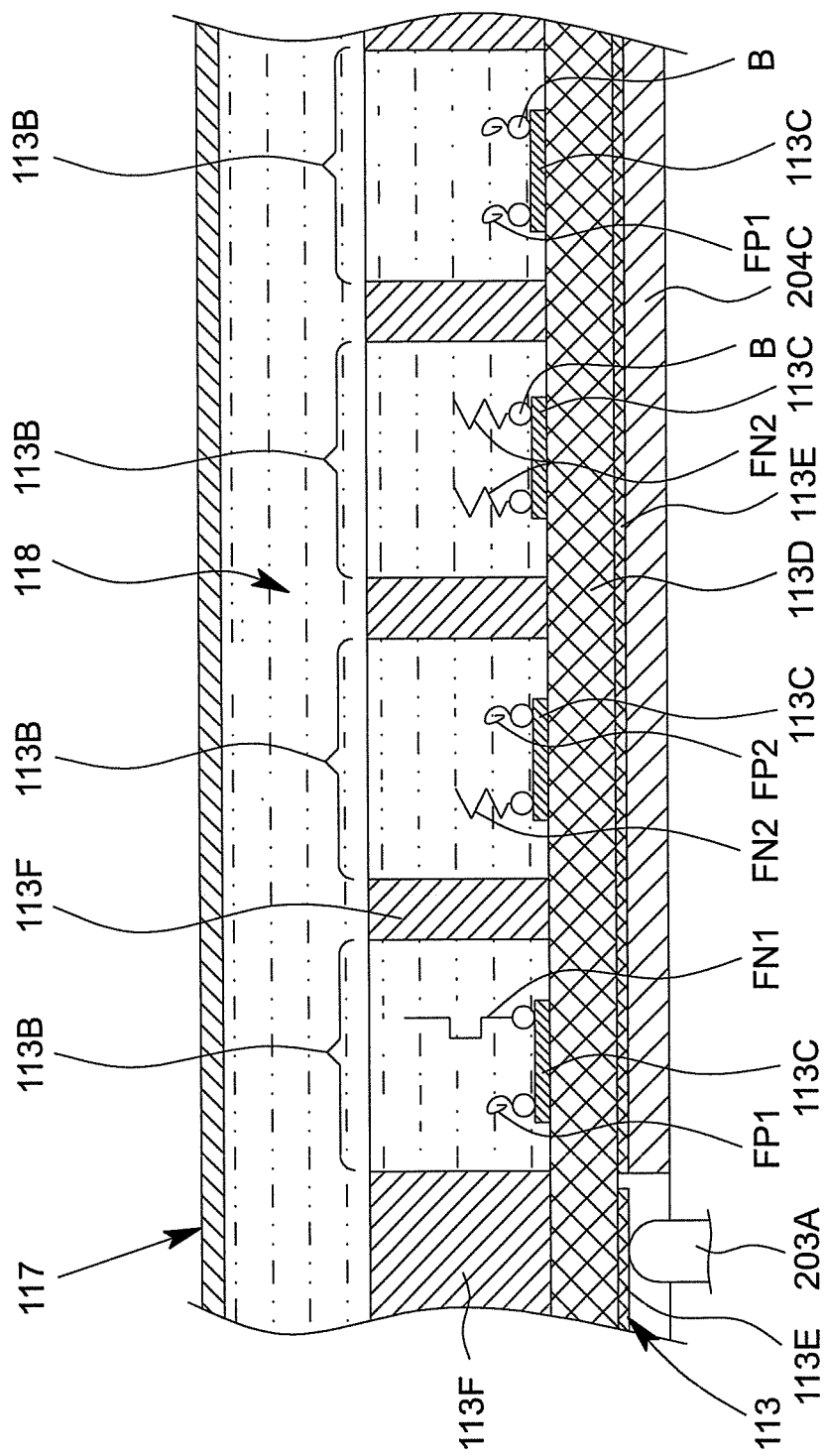
FIG. 8 is a schematic sectional view of the sensor arrangement after a protein assay has been carried out.

FIG. 8 is a schematic sectional view of the sensor arrangement after the protein assay has been carried out and/or after the capture proteins FP and target proteins ZP have been denatured and the sensor compartment 118 has been flushed. In the state shown, the sensor arrangement is thus prepared for the nucleic-acid assay, in particular such that the nucleic-acid assay can be carried out and/or the target nucleic-acid sequences ZN can be fed to the sensor compartment 118.

As shown in FIG. 8, after the protein assay has been carried out and after the subsequent addition of heat the capture nucleic-acid sequences FN are intact and only the capture proteins FP are denatured and/or destroyed.

A nucleic-acid assay is preferably carried out after the preferred denaturing of the capture proteins FP. The sample is first prepared for this purpose.

Preferably, the sample P or a portion thereof is removed for the nucleic-acid assay, optionally via the outlet 104C or the intermediate connection 104D of the receiving cavity 104, as already explained.

Preferably, the sample P or a portion thereof for the nucleic-acid assay in the cartridge 100 is metered, in particular in or by means of the first metering cavity 105A and/or second metering cavity 105B, before being introduced into the mixing cavity 107. Here, in particular the upstream and/or downstream sensor portions 116 are used together with the assigned sensors 206 in order to make possible the desired metering, as already explained for the protein assay.

After the metering, a sample portion for the nucleic-acid assay is present in the mixing cavity 107.

In the mixing cavity 107, the sample P or sample portion for the nucleic-acid assay is preferably prepared for further analysis and/or is mixed with a reagent, preferably with a liquid reagent F1 from a first storage cavity 108A and/or with one or more dry reagents S1, S2 and/or S3, which are optionally provided in the mixing cavity 107.

The liquid and/or dry reagents can be introduced into the mixing cavity 107 before and/or after the sample P. In the example shown, the dry reagents S1 to S3 are preferably introduced into the mixing cavity 107 previously and are optionally dissolved by the sample P and/or the liquid reagent F1.

The liquid reagent F1 may be a reagent, in particular a PCR master mix for the amplification reaction or PCR, and/or may be a sample buffer. Preferably, the PCR master mix contains nuclease-free water, enzymes for carrying out the PCR, in particular at least one DNA polymerase, nucleoside triphosphates (NTPs), in particular deoxynucleotides (dNTPs), salts, in particular magnesium chloride, and/or reaction buffers.

The dry reagents S1, S2 and/or S3 may likewise be reagents required for carrying out an amplification reaction or PCR, which are in a dry, in particular lyophilised, form. Preferably, the dry reagents S1, S2 and/or S3 are selected in particular from lyophilised enzymes, preferably DNA polymerases, NTPs, dNTPs and/or salts, preferably magnesium chloride.

The dissolving or mixing in the mixing cavity 107 takes place or is assisted in particular by introducing and/or blowing in gas or air, in particular from the bottom. This is carried out in particular by accordingly pumping gas or air in the circuit by means of the pump or pump apparatus 112.

Subsequently, a desired volume of the sample P that is mixed and/or pretreated in the mixing cavity 107 is preferably fed to one or more reaction cavities 109, particularly preferably via (respectively) one of the, optional intermediate cavities 106A to 106C arranged before or upstream of the respective reaction cavities 109 and/or with different reagents or primers, in this case dry reagents S4 to S6, being added or dissolved.

In contrast to the protein assay, during the nucleic-acid assay the sample P or a portion thereof is removed from the mixing cavity 107 and fed to the sensor arrangement and/or sensor apparatus 113 via the reaction cavities 109 and/or the intermediate temperature-control cavity 110.

Particularly preferably, the (premixed) sample P is split into several sample portions, preferably of equal size, and/or is divided between the intermediate cavities 106A to 106C and/or reaction cavities 109, preferably evenly and/or in sample portions of equal size.

Different reagents, in the present case dry reagents S4 to S6, particularly preferably primers, in particular those required for the PCR or PCRs, in particular groups of different primers in this case, are preferably added to the (premixed) sample P or the sample portions in the intermediate cavities 106A to 106C and/or different reaction cavities 109, respectively.

The primers in the different groups or sample portions differ in particular in terms of the hybridization temperatures of the amplification products generated by the respective primers.

Particularly preferably, marker primers are used in the sense already specified at the outset.

In the embodiment shown, the reagents or primers S4 to S6 are contained in the intermediate cavities 106A to 106C. However, other solutions are also possible, in particular those in which the reagents or primers S4 to S6 are contained in the reaction cavities 109.

According to a preferred embodiment, the intermediate cavities 106A to 106C each contain primers for amplifying/copying one analyte, preferably two different analytes and more preferably three different analytes. However, it is also possible for four or more different analytes to be amplified/copied per reaction cavity 109 or sample portion.

Particularly preferably, the reaction cavities 109 are filled in succession with a specified volume of the (pretreated) sample P or with respective sample portions via the intermediate cavities 1064 to 106C that are each arranged upstream of the respective reaction cavities 109. For example, the first reaction cavity 109A is filled with a specified volume of the pretreated sample P before the second reaction cavity 109B and/or the second reaction cavity 109B is filled therewith before the third reaction cavity 109C.

In the reaction cavities 109, the amplification reactions or PCRs are carried out to copy/amplify the analytes or target nucleic-acid sequences ZN. This is carried out in particular by means of the assigned, preferably common, reaction temperature-control apparatus(es) 204A and/or preferably simultaneously for all the reaction cavities 109, i.e. in particular using the same cycles and/or temperature (curves/profiles).

The PCR or PCRs are carried out on the basis of protocols or temperature profiles that are essentially known to a person skilled in the art. In particular, the mixture or sample volume located in the reaction cavities 109 is preferably cyclically heated and cooled.

Preferably, nucleic-acid products and/or target nucleic-acid sequences ZN are produced from the analytes as amplification products in the reaction cavity/cavities 109.

During the nucleic-acid assay, the label L is in particular produced directly and/or during the amplification reaction(s) (in each case) and/or is attached to the analytes, amplification products and/or target nucleic-acid sequences ZN. This is in particular achieved by using corresponding, preferably biotinylated, primers. However, the label L can also be produced and/or bonded to the analytes, amplification products, target nucleic-acid sequences ZN and/or target proteins ZP separately or later, optionally also only in the sensor compartment 118 and/or after hybridisation.

In particular, during the protein assay, a label L is only bonded to analytes and/or target proteins ZP after hybridization of the analytes and/or target proteins ZP to the capture molecules.

The label L is used in particular for detecting bonded analytes and/or amplification products. In particular, the label L can be detected or the label L can be identified in a detection process, as explained in greater detail in the following.

Particularly preferably, during the nucleic-acid assay it is provided for a plurality of amplification reactions or PCRs to be carried out in parallel or independently from one another using different primers S4 to S6 and/or primer pairs, such that a large number of (different) analytes or target nucleic-acid sequences ZN can be amplified or copied in parallel and subsequently analyzed.

After carrying out the amplification reaction(s), corresponding fluid volumes and/or sample portions and/or amplification products are conducted out of the reaction cavities 109 in succession to the sensor arrangement, in particular the sensor apparatus 113 and/or the sensor compartment 118, in particular via a group-specific and/or separate intermediate cavity 106E, 106F or 106G (respectively) and/or via the optional (common) intermediate temperature-control cavity 110.

The intermediate cavities 106E to 106G may contain further reagents, in this case dry reagents S9 and S10, respectively, for preparing the amplification products for the hybridization, e.g., a buffer, in particular an SSC buffer, and/or salts for further conditioning. On this basis, further conditioning of the amplification products can be carried out, in particular in order to improve the efficiency of the subsequent hybridization (bonding to the capture molecules). Particularly preferably, the pH of the sample P is set or optimized in the intermediate cavities 106E to 106G and/or by means of the dry reagents S9 and S10.

Optionally, the sample P or sample portions, the analytes, amplification products and/or target nucleic-acid sequences ZN is/are, in particular immediately before being fed to the sensor arrangement or sensor apparatus 113 and/or between the reaction cavities 109 and the sensor arrangement or sensor apparatus 113, actively temperature-controlled (in advance), preferably preheated, in particular by means of and/or in the intermediate temperature-control cavity 110 and/or by means of the intermediate temperature-control apparatus 204B, particularly preferably in order to denature the analytes, amplification products and/or target nucleic-acid sequences ZN.

Preferably, the capture proteins FN and target proteins ZP from the protein assay carried out previously are denatured by means of feeding in the sample P or sample portion for the nucleic-acid assay that has been heated by means of and/or in the intermediate temperature-control cavity 110 and/or by means of the intermediate temperature-control apparatus 204B, as already explained.

After the (heated) sample P and/or the analytes and/or amplification products are fed to the sensor apparatus 113, the analytes and/or amplification products are hybridised to the capture nucleic-acid sequences FN, preferably by (actively) temperature-controlling, in particular heating, the sensor arrangement or sensor apparatus 113, in particular by means of the sensor temperature-control apparatus 204C, as shown in FIG. 9.

Once the sample P, analytes and/or amplification products are hybridised and/or bonded to the capture nucleic-acid sequences FN, detection follows, in particular by means of the preferably provided label L, or in another manner.

In the following, a particularly preferred variant of the detection is described in greater detail, specifically electrochemical detection or detection by means of redox cycling, but other types of detection, for example optical or capacitive detection, may also be carried out. The detection described in the following is preferably carried out both during the protein assay and/or aptamer assay, and during the nucleic-acid assay, and therefore the following explanations apply to all the assays.

Following the (respective) bondings/hybridizations of the analytes, the sensor arrangement and/or sensor apparatus 113 is prepared and/or pretreated for the detection.

Following the bonding of the analytes, preferably an optional washing process takes place and/or additional reagents or liquids, in particular from the storage cavities 108B to 108E, are optionally fed in.

In particular, it may be provided that remnants of the sample P, sample residues, or unbonded analytes or amplification products, reagents and/or remnants from the PCR, and other substances that may disrupt the further method sequence, are in particular removed from the sensor compartment 118.

Particularly preferably, a washing process for the sensor arrangement or sensor apparatus 113 is a process and/or method step in which a fluid, in particular a wash buffer, is conducted through the sensor compartment 118 and/or past the sensor apparatus 113, in particular in order to wash away or flush out unbonded analytes from the sensor compartment 118 and/or the region of the sensor apparatus 113. In this case, the wash buffer itself preferably does not comprise any analytes, and therefore the sensor compartment 118 is freed of substances that could prevent or distort a subsequent evaluation.

Washing or flushing may in particular take place using a fluid or reagent F3, in particular a wash buffer, particularly preferably a sodium-citrate buffer or SSC buffer, which is preferably contained in the storage cavity 108C. Unbonded analytes, amplification products and substances which could disrupt subsequent detection are preferably removed from the sensor compartment 118 and/or from the sensor apparatus 113 by the wash buffer and/or fed to the collection cavity 111.

Subsequently and/or after the washing process, in accordance with a preferred variant of the method, detection of the analytes and/or amplification products bonded to the capture molecules takes place.

If the bonded analytes or amplification products are still not marked or not provided with a label L, as in the protein assay, the labels L are then fed to the sensor arrangement or the sensor compartment 118, preferably from the storage cavity 108E, particularly preferably in the form of a liquid reagent F5. Optionally, there is then another washing process.

In order to detect the analytes or amplification products bonded to the capture molecules, a reagent F4 and/or detector molecules D, in particular alkaline phosphatase/streptavidin, is/are fed to the sensor apparatus 113, preferably from the storage cavity 108D.

Within the meaning of the present invention, the term "detector molecules" is preferably understood to mean molecules that bond specifically to the marker or label L of the (bonded) analytes or amplification products and thus allow the detection thereof.

In particular, the detector molecules D may be enzyme conjugates and/or immunoconjugates, which bond specifically to the marker or label L, in particular biotin, and comprise a reporter enzyme for converting a substrate SU.

In the context of the present invention, the detector molecules D are preferably based on streptavidin, which has a high affinity for biotin, and/or alkaline phosphatase, which can convert non-reactive phosphate monoesters to electrochemically active molecules and phosphate.

Preferably, a detection system is used, where the label L is based on biotin and where the detector molecules D are based on streptavidin/alkaline phosphatase. However, other detector molecules D can also be used.

The reagents F4 or detector molecules D can bond to the bonded analytes or amplification products, in particular to the label L of the bonded analytes or amplification products, particularly preferably to the biotin marker, as shown in FIG. 9.

Optionally, subsequently or after the reagents F4 and/or detector molecules D have bonded to the analytes and/or amplification products or the labels L, an (additional) washing process and/or flushing takes place, preferably by means of the fluid or reagent F3 or wash buffer, in particular in order to remove unbonded reagents F4 and/or detector molecules D from the sensor apparatus 113.

Preferably, a reagent S7 and/or S8 and/or substrate SU for the detection, in particular from the storage cavity 106D, is lastly fed to the sensor arrangement or sensor apparatus 113, preferably together with a fluid or reagent F2 (in particular a buffer), which is suitable for the substrate SU, particularly preferably for dissolving the reagent S7 and/or S8 and/or substrate SU, the fluid or reagent F2 in particular taken from the storage cavity 108B. In particular, the reagent S7 and/or S8 can form or can comprise the substrate SU.

Preferably, p-aminophenyl phosphate (pAPP) is used as the substrate SU.

The substrate SU preferably reacts on and/or with the bonded analytes or amplification products and/or detector molecules D and/or allows these to be electrochemically measured.

In order to carry out the detection or electrochemical measurement of the bonded analytes or amplification products or after adding the substrate SU, the sensor cover 117 is preferably pneumatically actuated and/or lowered onto the sensor apparatus 113 (as shown in FIG. 7 for the protein assay), in particular in order to fluidically separate the (individual) sensor fields 113B from one another, and/or to prevent or minimise the exchange of substances between the sensor fields 113B.

Actuating or lowering the sensor cover 117 in particular prevents a reaction and/or detection from being assigned to an incorrect or adjacent sensor field 113B, and in this way prevents measurement inaccuracies or errors from occurring. In particular, the sensor cover 117 increases the measurement accuracy of the method.

As shown in particular in FIG. 7 for the protein assay, the substrate SU is preferably split by the bonded detector molecules D, in particular the alkaline phosphatase of the bonded detector molecules D, preferably into a first substance SA, such as p-aminophenol, which is in particular electrochemically active and/or redox active, and a second substance SP, such as phosphate.

Preferably, the first or electrochemically active substance SA is detected in the sensor apparatus 113 or in the individual sensor fields 113B by electrochemical measurement and/or redox cycling.

Particularly preferably, by means of the first substance SA, a redox reaction takes place at the electrodes 113C, the first substance SA preferably discharging electrons to or receiving electrons from the electrodes 113C.

In particular, the presence of the first substance SA and/or the respective amounts in the respective sensor fields 113B is detected by the associated redox reactions. In this way, it can be determined qualitatively and in particular also quantitatively whether and how many analytes or amplification products are bonded to the capture molecules in the respective sensor fields 113B. This accordingly gives information on which analytes are or were present in the sample P, and in particular also gives information on the quantity of said analytes.

In particular, by means of the redox reaction with the first substance SA, an electrical signal is generated at the assigned electrodes 113C, the signal preferably being detected by means of an assigned electronic circuit.

Depending on the signal from the electrodes 113C that is generated in this way, it is determined whether and/or where hybridisation to the capture molecules has occurred.

The measurement is preferably carried out once for the protein assay and/or aptamer assay, and once for the nucleic-acid assay.

As already explained, the protein assay and the nucleic-acid assay are preferably carried out independently and/or in succession. In particular, the nucleic-acid assay is started only after the protein assay is complete, and/or the sample P or sample portions for the nucleic-acid assay is/are discharged from the receiving cavity 104 or mixing cavity 107 and/or fed to the reaction cavity/cavities 109 only after the protein assay has ended and/or after detection of the bonded target proteins ZP is complete.

Variants of the method are also possible, however, in which the protein assay and the nucleic-acid assay are started at the same time and/or overlap in time.

In a particularly preferred variant of the method, prior to and/or during hybridization and/or detection of the target proteins ZP, the target nucleic-acid sequences ZN are prepared for the amplification reactions, fed to the reaction cavities 109, prepared in the intermediate cavities 106 in particular for hybridization, and/or preheated in the intermediate temperature-control cavity 110. The duration of the test and/or the time for carrying out both the assays can be advantageously reduced in this manner.

Preferably, the target nucleic-acid sequences ZN are amplified in the reaction cavity/cavities 109 by means of the amplification reactions only after the protein assay has been carried out and/or in order to carry out the nucleic-acid assay. However, variants of the method are also possible in which amplification of the target nucleic-acid sequences ZN occurs or starts while the protein assay is still being carried out.

Preferably, the target nucleic-acid sequences ZN are fed to the sensor apparatus 113 and/or the sensor compartment 118, bonded to the corresponding capture nucleic-acid sequences FN and/or identified or detected in particular electrochemically and/or by redox cycling, as already explained, only after the protein assay has been carried out and/or after the capture proteins FP and/or target proteins ZP have been denatured.

FIG. 9 shows the sensor arrangement while the nucleic-acid assay is being carried out and/or immediately before the sensor cover 117 is lowered and/or immediately before detection of the target nucleic-acid sequences ZN that are bonded to the capture nucleic-acid sequences FN.

It is therefore possible, by means of the proposed method, to bond a plurality of, in particular, also different target proteins ZP, and a plurality of, in particular, also different target nucleic-acid sequences ZN, preferably sequentially and/or in succession, in one (common) sensor field 113B of the sensor apparatus 113 and/or of the sensor array 113A, in particular on one (common) electrode 113C of the sensor apparatus 113 and/or of the sensor array 113A, to the corresponding capture molecules, in particular the corresponding capture proteins FP and the corresponding capture nucleic-acid sequences FN.

The test results or measurement results, in particular of both the protein assay and the nucleic-acid assay, are in particular electrically transmitted to the analysis device 200 or the control apparatus 207 thereof, preferably by means of the electrical connection apparatus 203 and/or sequentially or simultaneously, and are accordingly prepared, analyzed, stored, displayed and/or output, in particular by the display apparatus 209 and/or interface 210.

After the test has been carried out, the cartridge 100 is disconnected from the analysis device 200 and/or is released or ejected therefrom, and is in particular disposed of.

Figure 10A:
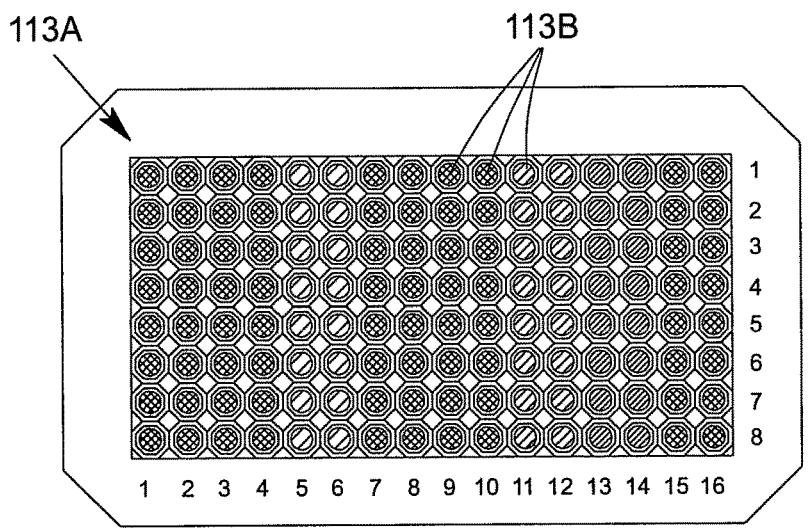
FIG. 10A is a schematic representation of the occupancy of sensor fields of a sensor array of the sensor apparatus.
Figure 10B:
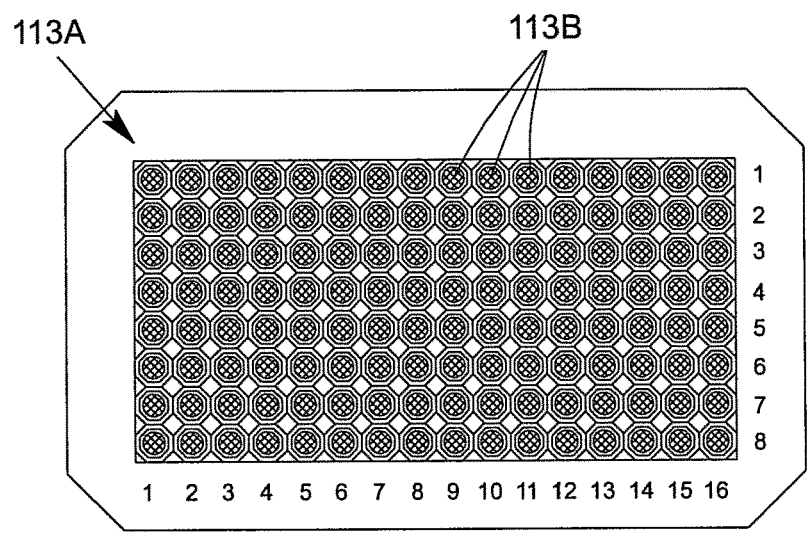
FIG. 10B is a schematic representation, corresponding to FIG. 10A, of a fluorescence measurement of the sensor fields.
Figure 10C:
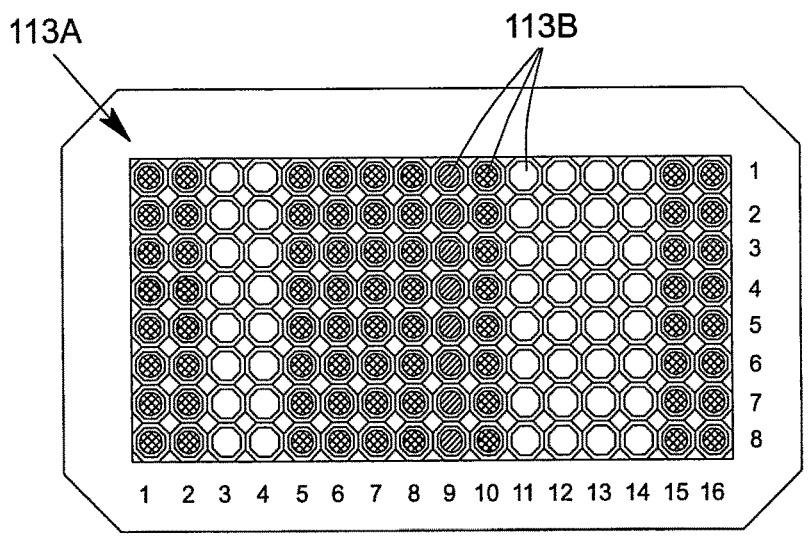
FIG. 10C is a schematic representation, corresponding to FIG. 10A, of another fluorescence measurement of the sensor fields.

FIG. 10A to 10C are schematic representations of completed fluorescence measurements on the proposed sensor array 113A.

The sensor array 113A comprises 128 sensor fields 113B which are arranged in eight rows and sixteen columns.

The sensor fields 113B in columns 1, 2 and 10 of the sensor array 113A are used as negative controls and do not contain any capture molecules, but instead are occupied only by a first sample buffer that is otherwise used for spotting, i.e. application in liquid form as small drops, of nucleic-acid sequences and/or oligonucleotides.

The sensor fields 113B in columns 3 and 4 of the sensor array 113A comprise capture nucleic-acid sequences FN based on a single-stranded DNA probe.

The sensor fields 113B in columns 5 and 6 of the sensor array 113A comprise capture proteins FP based on antibodies against adrenocorticotropic hormone (ACTH).

The sensor fields 113B in columns 7, 8, 15 and 16 of the sensor array are used as negative controls and do not contain any capture molecules, but instead only a sample buffer that is otherwise used for spotting proteins.

The sensor fields 113B in column 9 of the sensor array 113A are used as positive controls and comprise a biotinylated DNA probe.

The sensor fields 113B in columns 11 and 12 of the sensor array 113A comprise capture nucleic-acid sequences FN based on the single-stranded DNA probe, as in columns 3 and 4, and also capture proteins FP based on antibodies against adrenocorticotropic hormone (ACTH), as in columns 5 and 6, the first sample buffer having been used for spotting. The sensor fields 113B in columns 13 and 14 of the sensor array 113A likewise comprise capture nucleic-acid sequences FN based on the single-stranded DNA probe, as in columns 3 and 4, and capture proteins FP based on antibodies against adrenocorticotropic hormone (ACTH), as in columns 5 and 6, the second sample buffer having been used for spotting.

The sensor array 113A according to FIG. 10 was first used to carry out a protein assay for detecting ACTH, and subsequently used to carry out a nucleic-acid assay.

A protein assay for detecting adrenocorticotropic hormone (ACTH) was first carried out in the analysis system 1 using the sensor array 113B, which hormone was fed, as the target protein ZP, to the sensor apparatus 113 comprising the sensor array 113A. As shown in FIG. 10A, significant fluorescence could be measured in the sensor fields 113B in columns 5 and 6, which comprised antibodies directed against ACTH as capture proteins FP. Significant fluorescence could also be measured in the sensor fields 113B in columns 11 to 14, which contained both capture proteins FP specific to ACTH and additional capture nucleic-acid sequences FN that do not interact with ACTH, said fluorescence being lower in columns 13 and 14 than in columns 5, 6, 11 and 12. No fluorescence was measured in the remaining columns.

After the protein assay for detecting ACTH had been carried out, the proteins, i.e., both the capture proteins FP and the target proteins ZP and/or the complexes formed thereby, were denatured by heating the sensor apparatus 113 and/or capture proteins FP to temperatures of greater than 90° C. for more than 1 sec. After the temperature increase and/or denaturing of the proteins had been carried out, fluorescence could no longer be identified on the sensor apparatus 113, as shown in FIG. 10B.

Subsequently, a nucleic-acid assay was carried out on the same sensor apparatus 113. DNA strands complementary thereto were used as target nucleic-acid sequences ZN, which strands were marked with biotin and could hybridize to the DNA probe. The immobilized target nucleic-acid sequences ZN were detected using Alexa 647 streptavidin. Strong fluorescence could be measured in the sensor fields 113B in columns 3 and 4, which contained only capture nucleic-acid sequences FN as capture molecules. Significant, even similarly strong, fluorescence could also be measured in columns 11 to 14, which also contained capture proteins FP in addition to the capture nucleic-acid sequences FN. Fluorescence was also measured in the sensor fields 113B in column 9, which contained a biotinylated DNA probe as a positive control, although said fluorescence was somewhat lower.

The fluorescence measurements carried out show that first a protein assay (in the tests with just one analyte and/or target protein ZP) and subsequently, after the, preferably provided, denaturing by the effect of heat, a nucleic-acid assay (in this case with just one analyte and/or with just one target nucleic-acid sequence ZN) can be carried out using the analysis system 1 and/or cartridge 100 and/or sensor apparatus 113. The negative controls and positive controls have shown that the detection and the assays function in the desired manner.

The sensor apparatus 113 and/or sensor array 113A having the stated occupancy were not only checked by means of fluorescence measurements, however, but also subjected to electrochemical measurements, as explained in the following with reference to FIGS. 11A, 11B and 11C. These figures are each a graphical representation of the measured values that have resulted from the electrochemical measurements.

The electrochemical measurements were carried out in the manner already explained, in particular with reference to FIGS. 6 to 9.

The diagrams each show the sensor fields 113B arranged in eight rows (right-hand axis 1 to 8) and sixteen columns (top axis V1 to V16), and the current or power measurement curves resulting in each case (the bottom axis shows the time in sec, and the left-hand column shows the measured current or power in values proportional thereto).

An increase in the current or power and/or the signal intensity indicates splitting of the substrate p-aminophenyl phosphate to p-aminophenol, which is redox-active and thus leads to the increase in the measurement signal.

Figure 11A:
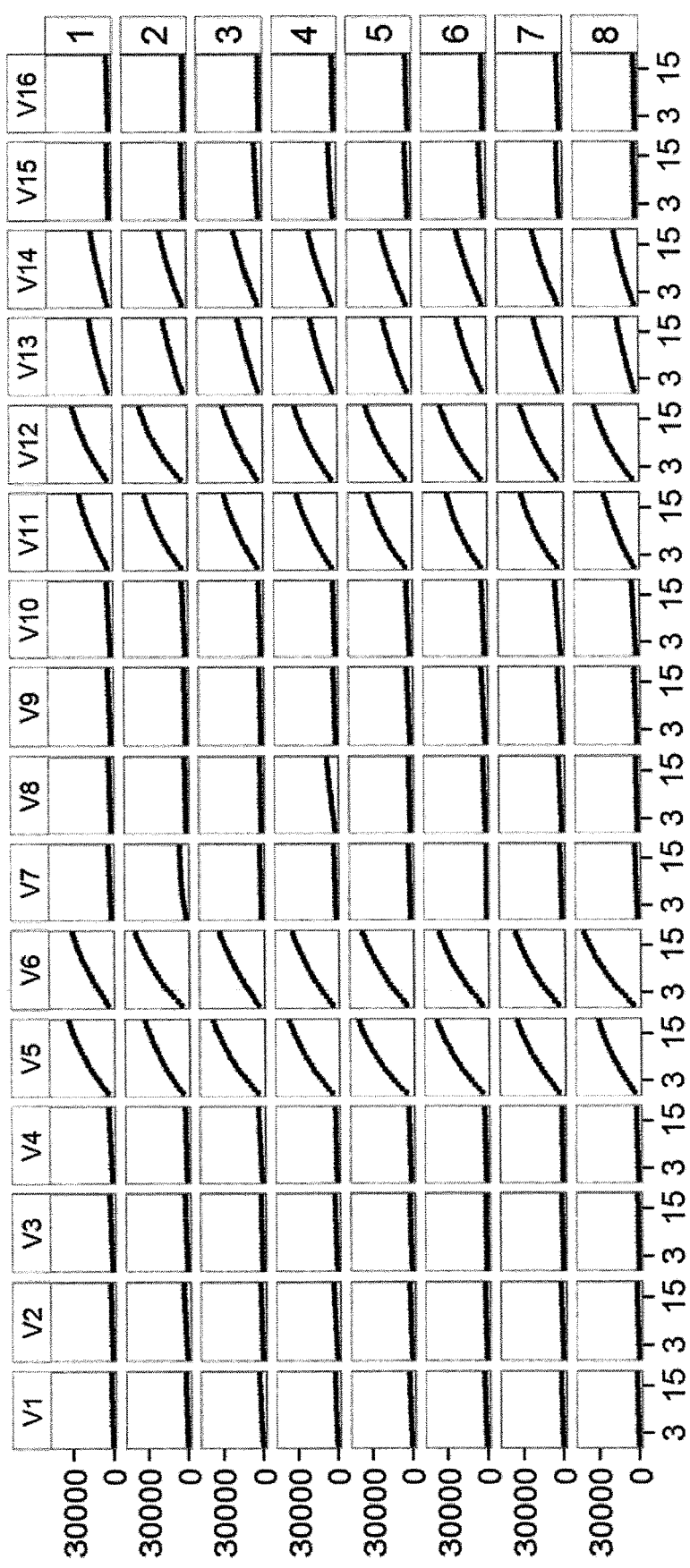
FIG. 11A is a graphical representation of a first electrochemical measurement of the sensor array.
Figure 11B:
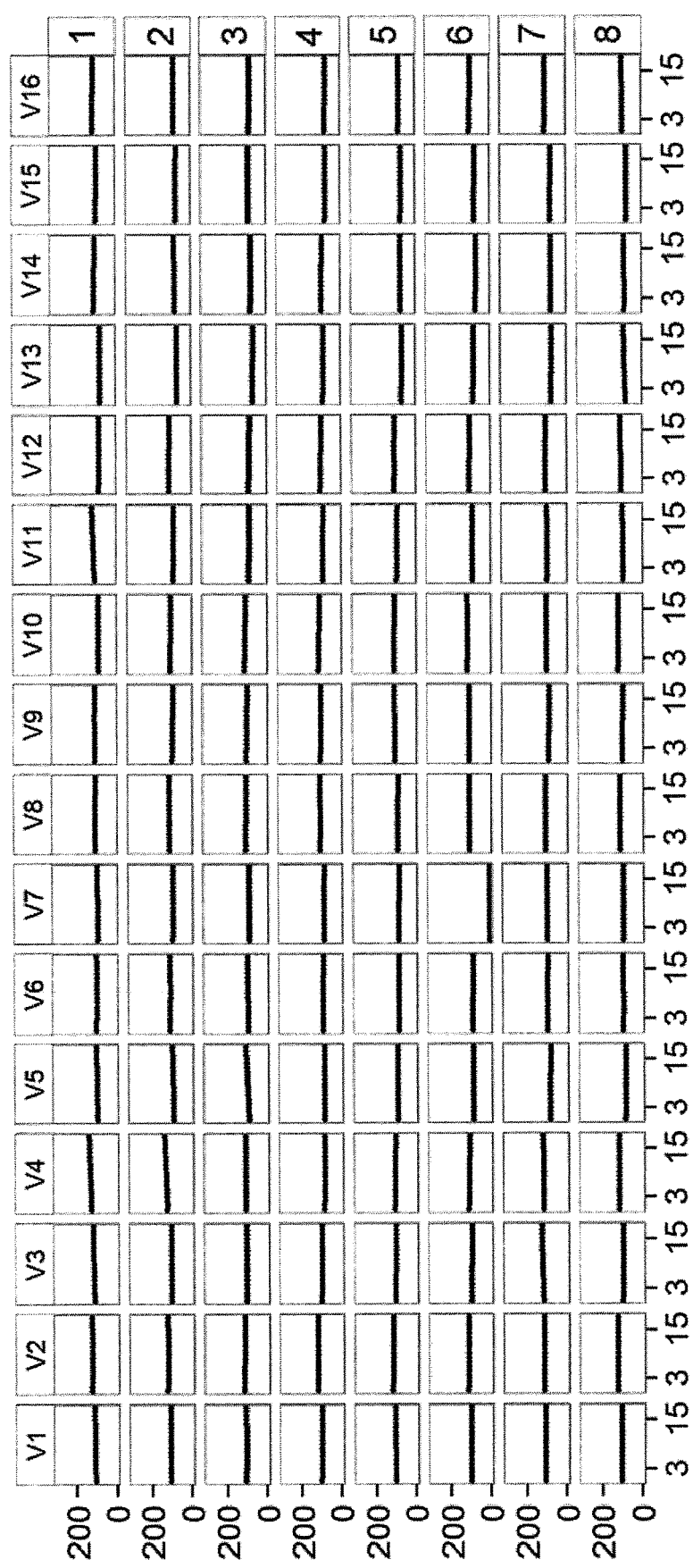
FIG. 11B is a graphical representation of a second electrochemical measurement of the sensor array.
Figure 11C:
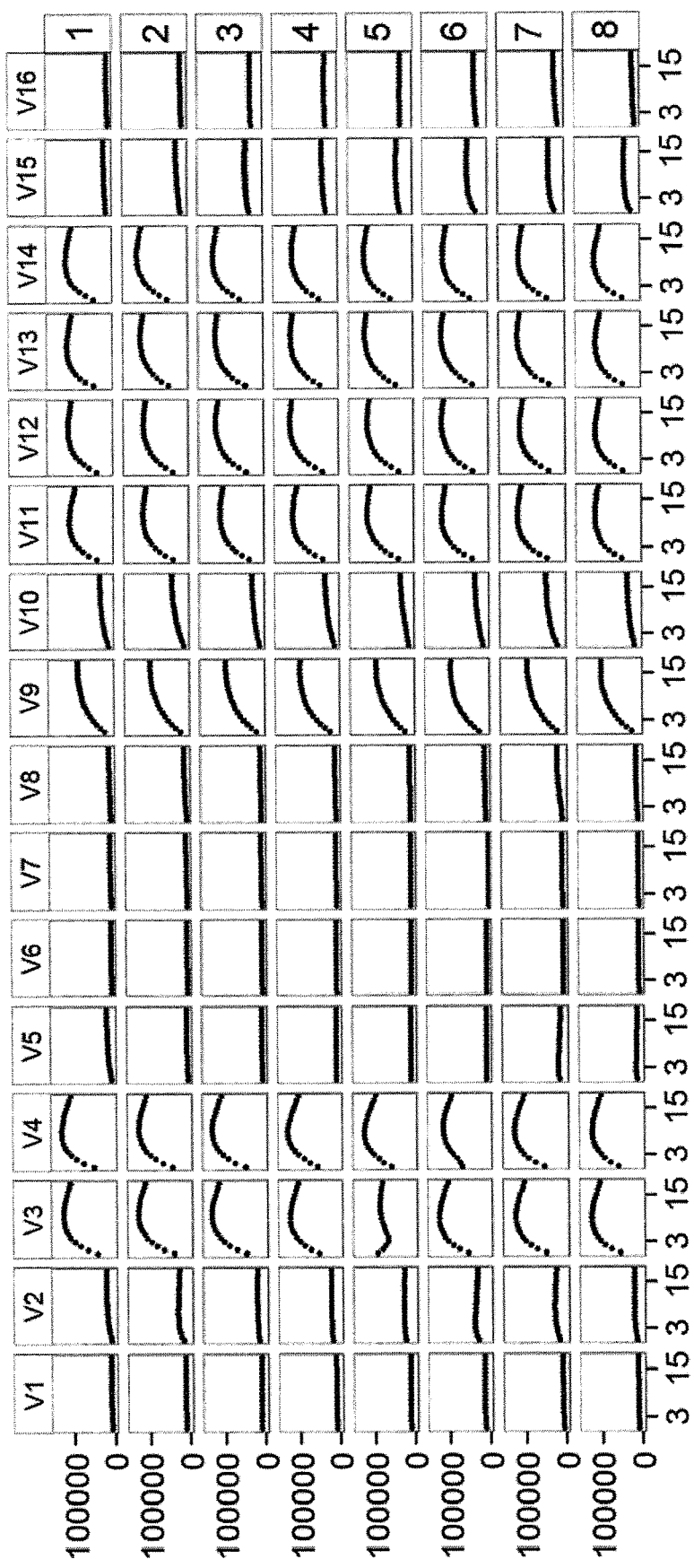
FIG. 11C is a graphical representation of a third electrochemical measurement of the sensor array.

FIG. 11A shows the electrochemical measurement of the protein assay for detecting ACTH, as already described in conjunction with FIG. 10A. Thus, significant conversion of p-aminophenyl phosphate to p-aminophenol was detected in the sensor fields 113B in columns 5 and 6, which only contained antibodies against ACTH as capture proteins FP, and in the sensor fields 113B in columns 11 to 14, which contained antibodies against ACTH as capture proteins FP and capture nucleic-acid sequences FN. The measurement results show that the measurement signals of the sensor fields 113B in columns V13 and V14 are smaller than in the sensor fields 113B in columns V11 and V12. This shows that the first sample buffer used for occupying and/or spotting the sensor fields 113B in columns V11 and V12 is more suitable and/or provides higher measurement results than when using the second sample buffer, as indicated by the lower measurement results for the sensor fields 113B in columns V13 and V14.

Following the protein assay, the proteins on the sensor array 113A were again denatured, and the conversion of p-aminophenyl phosphate to p-aminophenol was measured again. FIG. 11B shows the results of the electrochemical measurement following denaturing of the capture and target proteins at at least 90° C. for at least 1 sec. Due to denaturing the proteins and/or protein complexes, no further conversion of the substrate SU could take place during the subsequent redox cycling. With respect to FIG. 11B, it should be noted that the measured values and/or the current or power are shown here using a different scale, and the measurement signals measured were thus actually very small and/or negligible compared with the measurement signals that resulted in the sensor fields 113B in columns V5, V6 and V11 to V14 during the protein assay.

Following denaturing of the proteins, the same sensor apparatus 113 was used to carry out a nucleic-acid assay. FIG. 11C shows the results of the electrochemical measurement for detecting target nucleic-acid sequences ZN by means of the nucleic-acid assay. Significant substrate conversion could be measured both in the sensor fields 113B in columns 3 and 4, which comprised only the capture nucleic-acid sequences FN as the capture molecules, and in the sensor fields 113B in columns 11 to 14, which comprised both the capture proteins FP for ACTH and the capture nucleic-acid sequences FN. Substrate conversion could also be identified in the sensor fields 113B in column 9, which comprised a biotinylated DNA probe as a positive control. No relevant measurement signals could be detected in the sensor fields 113B that were used as a negative control and/or that only contained capture proteins FP for ACTH.

The embodiments show that both target proteins ZP and target nucleic-acid sequences ZN can be detected or identified in the same cartridge 100 and/or sensor apparatus 113, in particular also in common sensor fields 113B, on the basis of the proposed method and/or using the proposed analysis system 1 and/or analysis device 200 and the cartridge 100, and/or using the described sensor apparatus 113. It is thus proposed that a number of different samples P from different substance classes, in particular based on proteins on the one hand and nucleic-acid sequences on the other hand, can be very reliably analyzed and detected in a cartridge 100 and/or sensor apparatus 113.

On account of the possible multiple occupancy of individual sensor fields 113E with capture molecules of different substance classes, a significantly larger number of samples P and/or analytes can thus be reliably detected using just one sensor apparatus 113, which is in turn associated with improved method efficiency and a reduction in costs.

As already mentioned, different groups of capture molecules are preferably used for bonding and/or detecting in particular different kinds and/or types of target molecules and/or target analytes.

Preferably, capture aptamers FA could in principle also be used as capture molecules, in particular as a group of capture molecules, and particularly preferably together with other kinds and/or types of capture molecules and/or together with another group of capture molecules, particularly preferably together with capture proteins FP and/or capture nucleic-acid sequences FN.

FIG. 12 is a schematic sectional view, corresponding to FIG. 6, of another, preferred embodiment of the cartridge 100 and/or sensor apparatus 113, both capture aptamers FA and capture nucleic-acid sequences FN being provided and/or used as capture molecules. Preferably, different capture aptamers FA1 and FA2 are used here, in order to be able to bond and/or detect or identify different analytes.

Preferably, the sensor apparatus 113 comprises and/or individual sensor fields 113B comprise bonded capture aptamers FA as capture molecules, i.e. in particular a group of, preferably different, capture aptamers FA1, FA2 as capture molecules, here in particular together with a group of capture nucleic-acid sequences FN1, FN2. However, other combinations are also possible. In particular, the capture aptamers FA can also be used as capture molecules independently from other capture molecules.

The capture aptamers FA particularly preferably bond corresponding target proteins ZP as analytes. However, capture aptamers FA can in principle also bond other target analytes, in particular short molecules, such as steroids, but also other low-molecular substances, in particular from the field of environmental analytics, such as organophosphates or the like, as analytes.

As already explained, according to a second, particularly preferred variant of the method, a nucleic-acid assay for detecting or identifying a target nucleic-acid sequence ZN and an aptamer assay for detecting or identifying a target protein ZP or another target analyte are carried out, in particular sequentially and/or in the same cartridge 100 and/or sensor apparatus 113, the nucleic-acid assay preferably being carried out before the aptamer assay.

In the second variant of the method, a nucleic-acid assay is preferably carried out first. In this case, target nucleic-acid sequences ZN are bonded to the single-stranded DNA probes, i.e., to the capture nucleic-acid sequences FN, preferably at a hybridization temperature of approximately 50° C. to 60° C. Detection is carried out thereafter, preferably electrochemically, in particular by means of redox cycling, as already described. In this case, the temperature can be kept substantially the same or can even be lowered.

Subsequently, preferably a thermal effect and/or heating takes place, particularly preferably to above the hybridization temperature and/or threshold temperature, preferably to over 70° C., in particular over 80° C., particularly preferably over 90° C. or 100° C., in order to thermally activate and/or fold the capture aptamers FA, i.e., in particular, in order to cause the development of conformation. In other words, the capture aptamers FA become bondable only by means of thermal activation. However, other solutions are also possible here, in particular those in which the capture aptamers FA are already thermally activated in the delivery state of the cartridge 100.

Preferably, after conformation has been developed and/or after thermal activation, the temperature is only lowered again, in particular by active cooling, for example to less than 40° C., preferably by means of the temperature-control apparatus 204C, when the sample P or a sample portion or the target analytes, in particular target proteins ZP, is/are fed to the capture aptamers FA for bonding.

Subsequently, the corresponding target molecules and/or analytes can be bonded to the capture aptamers FA. In the example shown, in particular target proteins ZP and/or hormones, but optionally also steroids or other substances, preferably natural substances, are bonded.

Finally, the target analytes, in particular target proteins ZP or the like, bonded to the capture aptamers FA are detected. This is preferably again carried out electrochemically, in particular by means of redox cycling, as already described above in particular with respect to the protein assay.

Particularly preferably, a protein assay within the meaning already described and/or another assay for testing for other substances, in particular natural substances, such as lipids or steroids or the like, can thus also be carried out using the capture aptamers FA as capture molecules. Variants of the method are in particular also possible in which a protein assay for detecting a target protein ZP and an aptamer assay for detecting another target analyte that is in particular different from the target protein ZP can be carried out, in particular sequentially and/or in the same cartridge 100 and/or sensor apparatus 113.

Particularly preferably, by using capture aptamers FA as capture molecules for proteins or other substances, an aptamer assay can be carried out instead of the protein assay, in this case the nucleic-acid assay preferably being carried out before the aptamer assay.

Using capture aptamers FA, in particular in combination with capture nucleic-acid sequences FN and/or instead of capture proteins FP, makes it possible to achieve particularly good storage stability and/or thermal stability of the cartridge 100 and/or sensor apparatus 113. In particular, it is then not necessary to cool the cartridge 100 and/or sensor apparatus 113. Rather, the cartridge 100 and/or sensor apparatus 113 can also be heated in the meantime to a temperature above normal room temperature, in particular also to above 40° C. or 50° C., without the capture molecules being damaged.

As already explained at the outset, the capture aptamers FA are preferably produced synthetically such that they do not yet assume their actual three-dimensional structure, and therefore (one-off) heating to or above a threshold temperature, in particular of over 90° C. or 95° C., is first required in order to thermally activate the capture aptamers FA. Preferably, the capture aptamers FA then, in particular also when subsequently cooled, retain the provided three-dimensional structure that makes the capture aptamers FA capable of bonding the corresponding target molecules and/or analytes.

The capture aptamers are activated only after a corresponding thermal effect and/or heating, in particular only after the threshold temperature has been reached or exceeded. FIG. 12 schematically shows the capture aptamers FA when not yet folded, i.e. when deactivated and/or inactive.

According to another variant, it is also possible to use capture aptamers FA that are already thermally activated as capture molecules, which molecules no longer need to be thermally activated. In this case, preferably an aptamer assay is first carried out, using the capture aptamers FA as capture molecules and at a temperature significantly below the hybridisation temperature of the capture nucleic-acid sequences FN, and a nucleic-acid assay is carried out only thereafter. This is possible in particular when the nucleic-acid assay is carried out at an increased temperature of over 50° C. or 60° C., for example, at which the target analytes of the aptamer assay do not bond or are thermally labile. Accordingly, different combinations of assays and sequences are thus possible depending on the use of the different groups of capture molecules.

Particularly preferably, the analysis system 1 and/or cartridge 100 and/or sensor apparatus 113 is designed both for carrying out a protein assay and/or aptamer assay for detecting or identifying a target protein ZP, and for carrying out a nucleic-acid assay for detecting or identifying a target nucleic-acid sequence ZN.

In particular, the present invention relates also to any one of the following aspects which can be realized independently or in any combination, also in combination with any aspects described above or in the claims.

1. Analysis system 1 for testing, in particular, a biological sample P,
the analysis system 1 comprising a fluid system 103 having a plurality of channels 114 and a sensor apparatus 113 comprising capture molecules for bonding analytes of the sample P, characterised
in that the capture molecules are selected from at least two types from the selection group consisting of capture proteins FP, capture aptamers FA and/or capture nucleic-acid sequences FN, and/or
in that the sensor apparatus 113 comprises a first group of capture molecules FP, FA and a second group of capture molecules FN, the first group of capture molecules FP, FA being able to be thermally activated in order to bond analytes or thermally deactivated and/or denatured in order to prevent bonding of analytes, by means of a temperature-control apparatus 204B, 204C.

2. Method for testing an in particular biological sample P, analytes of the sample P being bonded to capture molecules of a sensor apparatus 113 and the bonded analytes being detected by means of the sensor apparatus 113, characterised
in that a plurality of assays selected from at least two assays from the selection group consisting of a protein assay, a nucleic-acid assay and/or an aptamer assay are carried out by means of the sensor apparatus 113, and/or
in that the sample P is received in a cartridge 100 and is split into portions, and a plurality of assays selected from at least two assays from the selection group consisting of a protein assay, a nucleic-acid assay and/or an aptamer assay are carried out in the same cartridge 100 and/or sensor apparatus 113, and/or in that both target proteins ZP and target nucleic-acid sequences ZN, as analytes of the sample P, are bonded to corresponding capture molecules in a common sensor array 113A of the sensor apparatus 113 and are detected, and/or
in that a group of capture molecules FP, FA is thermally activated so as to be able to bond analytes or is thermally deactivated and/or denatured so as not to bond any analytes, in particular one assay being carried out by means of the group of capture molecules FP, FA and another assay being carried out by another group of different capture molecules FN.

Individual aspects and features of the present invention and individual method steps and/or variants of the method may be implemented independently from one another, but also in any desired combination and/or order.

What is claimed is:

1. A method for testing a biological sample, comprising:
carrying out a plurality of assays selected from at least two assays from the selection group consisting of a protein assay, a nucleic-acid assay or an aptamer assay by means of a sensor apparatus having a plurality of sensor fields and electrodes, two electrodes forming one sensor field, each electrode comprising at least two types of capture molecules selected from the selection group consisting of capture proteins, capture nucleic-acid sequences and capture aptamers,
bonding of target analytes of the sample to capture molecules of the sensor apparatus, wherein different types of target analytes, in particular target proteins and target nucleic-acid sequences, are bonded to the corresponding capture molecules on each of the electrodes, and
detecting or identifying the bonded target analytes by means of the sensor apparatus.

2. The method according to claim 1, wherein the sample is received in a cartridge and is split into portions, and a plurality of assays selected from at least two assays from the selection group consisting of the protein assay, the nucleic-acid assay or the aptamer assay are carried out in the same cartridge or sensor apparatus.

3. The method according to claim 1, wherein a group of capture molecules is thermally activated so as to be able to bond analytes or is thermally deactivated or denatured so as not to bond any analytes.

4. The method according to claim 3, wherein one assay is carried out by means of the group of capture molecules and another assay being carried out by another group of different capture molecules.

5. The method according to claim 1, wherein the protein assay is carried out before the nucleic-acid assay.

6. The method according to claim 1, wherein the nucleic-acid assay is carried out before the aptamer assay.

7. The method according to claim 1, wherein at least one of the protein assay, the nucleic-acid assay or the aptamer assay is carried out in a common sensor array of the sensor apparatus.

8. The method according to claim 1, wherein, at least one of target analytes or target proteins are fed to the sensor apparatus via a fluid system having a plurality of channels.

9. The method according to claim 1, wherein at least one of target analytes or target proteins are bonded to corresponding capture proteins as capture molecules.

10. The method according to claim 1, further comprising detecting or identifying at least one of target analytes or target proteins at least one of electrochemically or by redox cycling.

11. The method according to claim 1, wherein capture proteins and at least one of target analytes or target proteins are bonded to one another are then denatured by the addition of heat after carrying out of at least one of detection or the protein assay has been carried out.

12. The method according to claim 1, wherein capture proteins and at least one of target analytes or target proteins are bonded to one another are then are removed from the sensor apparatus after at least one of detection or carrying out of the protein assay.

13. The method according to claim 1, wherein the sensor apparatus is heated after the protein assay has been carried out at a temperature of at least one of greater than 40° C. or less than 70° C.

14. The method according to claim 1, wherein target nucleic-acid sequences are amplified in a reaction cavity by means of an amplification reaction.

15. The method according to claim 1, wherein target nucleic-acid sequences are fed to the sensor apparatus via a fluid system having a plurality of channels.

16. The method according to claim 1, wherein the target nucleic-acid sequences are bonded to corresponding capture nucleic-acid sequences as capture molecules.

17. The method according to claim 1, wherein target nucleic-acid sequences are identified or detected electrochemically or by redox cycling.

18. The method according to claim 1, wherein a plurality of target proteins and a plurality of target nucleic-acid sequences are bonded to corresponding capture molecules in a common sensor field of the sensor apparatus and are detected or identified.

19. The method according to claim 1, wherein target proteins and target nucleic-acid sequences, as analytes of the sample, are bonded to the corresponding capture molecules on a common electrode of the plurality of electrodes.

20. The method according to claim 1, wherein target proteins are bonded to the corresponding capture proteins and detected, and only subsequently are the target nucleic-acid sequences bonded to the corresponding capture nucleic-acid sequences and detected.

21. The method according to claim 1, wherein after the end of the protein assay and/or in order to prepare the nucleic-acid assay, the sensor apparatus is heated, in particular to at least the denaturing temperature of the target proteins and/or capture proteins and/or to the temperature required for denaturing target proteins and capture proteins that are bonded to one another.

22. A method for testing a biological sample, comprising:
sequentially bonding of different types of target analytes of the sample to capture molecules of a sensor apparatus,
sequentially detecting or identifying the bonded target analytes by means of the sensor apparatus,
wherein target proteins as target analytes of the sample are bonded to corresponding capture proteins as capture molecules and detected,
wherein the capture proteins and target proteins bonded to one another are denatured by the addition of heat and removed from the sensor apparatus after detection, and
wherein target nucleic-acid sequences as target analytes of the sample are subsequently bonded to corresponding capture nucleic-acid sequences as capture molecules and are detected by means of the sensor apparatus.

23. The method according to claim 22, further comprising detecting or identifying at least one of target analytes or target proteins at least one of electrochemically or by redox cycling.

24. The method according to claim 22, wherein the sensor apparatus is heated after detection of the target proteins at a temperature of at least one of greater than 40° C. or less than 70° C.

25. The method according to claim 22, wherein a plurality of target proteins and a plurality of target nucleic-acid sequences are bonded to corresponding capture molecules in a common sensor field of the sensor apparatus and are detected or identified, the common sensor field being formed by at least two electrodes.

26. The method according to claim 22, wherein capture aptamers are thermally activated so as to be able to bond analytes after detection of the target proteins and/or target nucleic-acid sequences.

27. A method for testing a biological sample, comprising:
sequentially bonding of different types of target analytes of the sample to capture molecules of a sensor apparatus,
sequentially detecting or identifying the bonded target analytes by means of the sensor apparatus,
wherein target nucleic-acid sequences as target analytes of the sample are bonded to corresponding capture nucleic-acid sequences as capture molecules and are detected by means of the sensor apparatus,
wherein subsequently capture aptamers as capture molecules are thermally activated by the addition of heat in order to bond corresponding target analytes to the capture.

28. The method according to claim 27, wherein a plurality of target analytes is bonded to corresponding capture nucleic-acid sequences and corresponding capture aptamers in a common sensor field of the sensor apparatus and are detected or identified, the common sensor field being formed by at least two electrodes.

* * * * *